US012569498B2

(12) United States Patent
Casella

(10) Patent No.: US 12,569,498 B2
(45) Date of Patent: Mar. 10, 2026

(54) METHODS AND COMPOSITIONS FOR THE PREVENTION AND TREATMENT OF ISCHEMIA REPERFUSION INJURY AND INFECTION

(71) Applicant: CHILDREN'S NATIONAL MEDICAL CENTER, Washington, DC (US)

(72) Inventor: Daniel Casella, Alexandria, VA (US)

(73) Assignee: CHILDREN'S NATIONAL MEDICAL CENTER, Washington, DC (US)

(*) Notice: Subject to any disclaimer, the term of this patent is extended or adjusted under 35 U.S.C. 154(b) by 930 days.

(21) Appl. No.: 17/774,638

(22) PCT Filed: Nov. 6, 2020

(86) PCT No.: PCT/US2020/059267
§ 371 (c)(1),
(2) Date: May 5, 2022

(87) PCT Pub. No.: WO2021/092275
PCT Pub. Date: May 14, 2021

(65) Prior Publication Data

US 2022/0401453 A1 Dec. 22, 2022

Related U.S. Application Data

(60) Provisional application No. 62/931,522, filed on Nov. 6, 2019.

(51) Int. Cl.
*A61K 31/55* (2006.01)
*A61P 9/10* (2006.01)

(52) U.S. Cl.
CPC ................ *A61K 31/55* (2013.01); *A61P 9/10* (2018.01)

(58) Field of Classification Search
CPC .................................. A61K 31/55; A61P 9/10
See application file for complete search history.

(56) References Cited

U.S. PATENT DOCUMENTS

| | | | |
|---|---|---|---|
| 6,410,550 | B1 | 6/2002 | Coe |
| 6,890,927 | B2 | 5/2005 | Bogle |
| 2006/0019984 | A1 | 1/2006 | Groppi et al. |
| 2007/0232651 | A1 | 10/2007 | Habgood et al. |
| 2015/0094220 | A1 | 4/2015 | Cortijo Bringas et al. |

FOREIGN PATENT DOCUMENTS

| | | | |
|---|---|---|---|
| CN | 102580099 | A1 | 7/2012 |

OTHER PUBLICATIONS

Bodnar; J. Med. Chem. 2005, 48, 4, 905-908. https://doi.org/10.1021/jm049363q (Year: 2005).*
Xiong; Inflammation 2012, 35, 1357-1364. https://doi.org/10.1007/s10753-012-9449-2 (Year: 2012).*
Altavilla; Current Medicinal Chemistry, 2012, 19, 1219-1224. https://doi.org/10.2174/092986712799320538 (Year: 2012).*
Etter; Arch Intern Med. 2006, 166, 1553-1559. https://doi.org/10.1001/archinte.166.15.1553 (Year: 2006).*
Gigliotti; Journal of the American Society of Nephrology 2013, 1451-1460. https://doi.org/10.1681/ASN.2013010084 (Year: 2013).*
Hou; Biochemical and Biophysical Research Communications 2018, 500, 357-364. https://doi.org/10.1016/j.bbrc.2018.04.077 (Year: 2018).*
Karaguzel; Nat Rev Urol 2014, 11, 391-399. https://doi.org/10.1038/nrurol.2014.135 (Year: 2014).*
Minutoli; Endocrinology 2011, 152, 3852-3861. https://doi.org/10.1210/en.2011-1016 (Year: 2011).*
Yeboah; Kidney International 2008, 74, 62-69. https://doi.org/10.1038/ki.2008.94 (Year: 2008).*
International Search Report and Written Opinion in PCT/US2020/059267. Mailed Feb. 5, 2021. 18 pages.
Chen et al. Delayed Varenicline Administration Reduces Inflammation and Improves Forelimb 25-27 Use Following Exp Stroke. Journal of Stroke and Cerebrovascular Diseases : the Official Journal of National Stroke Association, Aug. 6, 2017.
Tryfonas, G. et al. Late postoperative results in males treated for testicular torsion during childhood. Journal of pediatric surgery. 1994;29:553-556.
Turner, T.T. et al. Acute testicular ischemia results in germ cell-specific apoptosis in the rat. Biology of reproduction. 1997;57:1267-1274.
Ulloa, L. The vagus nerve and the nicotinic anti-inflammatory pathway. Nature reviews. Drug discovery. 2005;4:673-684.
Van Westerloo, D.J. et al. The vagus nerve and nicotinic receptors modulate experimental pancreatitis severity in mice. Gastroenterology. 2006;130:1822-1830.
Visser, A.J. & Heyns, C.F. Testicular function after torsion of the spermatic cord. BJU international. 2003;92:200-203.
Wang, H. et al. Cholinergic agonists inhibit HMGB1 release and improve survival in experimental sepsis. Nature medicine. 2004;10:1216-1221.
Wei, S.M. et al. Probucol Reduces Testicular Torsion/Detorsion-Induced Ischemia/Reperfusion Injury in Rats. Oxid Med Cell Longev. 2017;2017:5424097.
Wei, S.M. et al. Beneficial effect of taurine on testicular ischemia-reperfusion injury in rats. Urology. 2007;70:1237-1242.
Wei, S.M. et al. Protective effect of rutin on testicular ischemia-reperfusion injury. Journal of pediatric surgery. 2011;46:1419-1424.

(Continued)

*Primary Examiner* — Daniel R Carcanague
(74) *Attorney, Agent, or Firm* — Meunier Carlin & Curfman LLC

(57) ABSTRACT

Disclosed herein are compositions for treating a subject with ischemia reperfusion injury or at risk of developing ischemia reperfusion injury, the method comprising administering to the subject an agonist of nicotinic cholinergic receptor α7nAchR. Also disclosed are methods and compositions for treating a subject with sepsis or at risk of developing an infection or sepsis, the method comprising administering to the subject an agonist of nicotinic cholinergic receptor α7nAchR. In one embodiment, the agonist of nicotinic cholinergic receptor α7nAchR is varenicline.

13 Claims, 14 Drawing Sheets

(56) References Cited

OTHER PUBLICATIONS

Yapanoglu, T. et al. Effect of etoricoxib on experimental oxidative testicular ischemia-reperfusion damage in rats induced with torsion-detorsion. Korean J Physiol Pharmacol. 2017;21:457-464.
Yoshikawa, H. et al. Nicotine inhibits the production of proinflammatory mediators in human monocytes by suppression of I-kappaB phosphorylation and nuclear factor-kappaB transcriptional activity through nicotinic acetylcholine receptor alpha7. Clin Exp Immunol. 2006;146:116-123.
Zhang, Guo-Qiang et al. "The effect of vitamin A on renal damage following acute pyelonephritis in children: a meta-analysis of randomized controlled trials." Pediatric Nephrology 31.3 (2016): 373-379.
Zhao, L.C. et al. Pediatric testicular torsion epidemiology using a national database: incidence, risk of orchiectomy and possible measures toward improving the quality of care. The Journal of urology. 2011;186:2009-2013.
Anderson, J.B. & Williamson, R.C. The fate of the human testes following unilateral torsion of the spermatic cord. British journal of urology. 1986;58:698-704.
Anderson, M.J. et al. Semen quality and endocrine parameters after acute testicular torsion. The Journal of urology. 1992;147:1545-1550.
Anderson, Ulf et al. Neural reflexes in inflammation and immunity. The Journal of Experimental Medicine. 2012; vol. 209 No. 6; 1057-1068.
Anthenelli, R.M. et al. Neuropsychiatric safety and efficacy of varenicline, bupropion, and nicotine patch in smokers with and without psychiatric disorders (EAGLES): a double-blind, randomised, placebo-controlled clinical trial. Lancet. 2016;387:2507-2520.
Bahat Özdoğan, E. et al. "Could Pyelonephritic Scarring Be Prevented by Anti-Inflammatory Treatment? An Experimental Model of Acute Pyelonephritis." BioMed Research International Jan. 2014 (2014): 134940.
Bille, J. & Glauser, M.P. "Protection against chronic pyelonephritis in rats by suppression of acute suppuration: effect of colchicine and neutropenia." The journal of infectious diseases 146.2 (1982): 220-226.
Bowen, S.E. et al. Interplay between vesicoureteric reflux and kidney infection in the development of reflux nephropathy in mice. Dis Model Mech. Jul. 2013;6(4):934-41. doi: 10.1242/dmm.011650. Epub Mar. 15, 2013. PMID: 23519031; PMCID: PMC3701213.
Caetano, G.F. et al. Comparison of collagen content in skin wounds evaluated by biochemical assay and by computer-aided histomorphometric analysis. Pharmaceutical biology. 2016;54:2555-2559.
Campling, B.G. et al. Acute activation, desensitization and smoldering activation of human acetylcholine receptors. PloS one. 2013;8:e79653.
Chen, Chih-Hao, et al. "Response of dermal fibroblasts to biochemical and physical cues in aligned polycaprolactone/silk fibroin nanofiber scaffolds for application in tendon tissue engineering." Nanomaterials 7.8 (2017): 219.
De Jonge, W.J. et al. Stimulation of the vagus nerve attenuates macrophage activation by activating the Jak2-STAT3 signaling pathway. Nature immunology. 2005;6:844-851.
Faessel, H.M. et al. Single-dose pharmacokinetics of varenicline, a selective nicotinic receptor partial agonist, in healthy smokers and nonsmokers. J Clin Pharmacol. Sep. 2006;46(9):991-8.
Faessel, H. et al. Pharmacokinetics, safety, and tolerability of varenicline in healthy adolescent smokers: a multicenter, randomized, double-blind, placebo-controlled, parallel-group study. Clin Ther. Jan. 2009;31(1):177-89. doi: 10.1016/j.clinthera.2009.01.003. PMID: 19243716.
Ghaffari, J. et al. "Assessment the effect of dexamethasone on urinary cytokines and renal scar in children with acute pyelonephritis." Iranian Journal of Kidney Diseases 13.4 (2019): 244.
Ghasemnejad-Berenji, M. et al. Rapamycin protects testes against germ cell apoptosis and oxidative stress induced by testicular ischemia-reperfusion. Iran J Basic Med Sci. 2017;20:905-911.
Gurocak, S. et al. "Renal tissue damage after experimental pyelonephritis: role of antioxidants and selective cyclooxygenase-2 inhibitors." Urology 76.2 (2010): 508-e1.
Hang, L. et al. "Interleukin-8 receptor knockout mice have subepithelial neutrophil entrapment and renal scarring following acute pyelonephritis." The Journal of infectious diseases 182.6 (2000): 1738-1748.
Hewitt, I.K. et al. Antibiotic Prophylaxis for Urinary Tract Infection-Related Renal Scarring: A Systematic Review. Pediatrics. May 2017;139(5):e20163145.
Huang, Ya-Yun et al. "Adjunctive oral methylprednisolone in pediatric acute pyelonephritis alleviates renal scarring." Pediatrics 128.3 (2011): e496-e504.
Huston, J.M. et al. Splenectomy inactivates the cholinergic antiinflammatory pathway during lethal endotoxemia and polymicrobial sepsis. The Journal of experimental medicine. 2006;203:1623-1628.
Imamoğlu, M. et al. Effects of melatonin on suppression of renal scarring in experimental model of pyelonephritis. Urology. Jun. 2006;67(6):1315-9. doi: 10.1016/j.urology.2005.12.013. Epub May 12, 2006. PMID: 16697444.
Jang, H. & Rabb, H. Immune cells in experimental acute kidney injury. Nat Rev Nephrol 11, 88-101 (2015).
Kalogeris, T. et al. (2014). "Mitochondrial reactive oxygen species: A double edged sword in ischemia/reperfusion vs preconditioning." Redox biology 2: 702-714.
Krarup T. The testes after torsion. British journal of urology. 1978;50:43-46.
Liu, J. et al. "Molecular characterization of the transition from acute to chronic kidney injury following ischemia/reperfusion." JCI insight 2.18 (2017): e94716.
Lysiak, J.J. et al. Peptide and nonpeptide reactive oxygen scavengers provide partial rescue of the testis after torsion. Journal of andrology. 2002;23:400-409.
Lysiak, J.J. et al. Essential role of neutrophils in germ cell-specific apoptosis following ischemia/reperfusion injury of the mouse testis. Biology of reproduction. 2001;65:718-725.
Meylan, P.R. et al. "Relationship between neutrophil-mediated oxidative injury during acute experimental pyelonephritis and chronic renal scarring." Infection and immunity 57.7 (1989): 2196-2202.
Murawski, I.J. et al. "The relationship between nephron No., kidney size and body weight in two inbred mouse strains." Organogenesis 6.3 (2010): 189-194.
Ning, J.Z. et al. MiR-29a Suppresses Spermatogenic Cell Apoptosis in Testicular Ischemia-Reperfusion Injury by Targeting TRPV4 Channels. Front Physiol. 2017;8:966.
Obach, R.S. et al. Metabolism and disposition of varenicline, a selective alpha4beta2 acetylcholine receptor partial agonist, in vivo and in vitro. Drug metabolism and disposition: the biological fate of chemicals. 2006;34:121-130.
Ozbek, O. et al. The protective effect of apocynin on testicular ischemia-reperfusion injury. The Journal of urology. 2015;193:1417-1422.
Parrish, W.R. et al. Modulation of TNF release by choline requires alpha7 subunit nicotinic acetylcholine receptor-mediated signaling. Molecular medicine (Cambridge, Mass.). 2008; 14:567-574.
Pohl, H.G. et al. "Adjunctive oral corticosteroids reduce renal scarring: the piglet model of reflux and acute experimental pyelonephritis." The Journal of urology 162.3 (1999): 815-820.
Qi, X. et al. Omega-3 polyunsaturated fatty acids ameliorates testicular ischemia-reperfusion injury through the induction of Nrf2 and inhibition of NF-KB in rats. Experimental and Molecular Pathology. 2017;103:44-50.
Rosas-Ballina, M. et al. Splenic nerve is required for cholinergic antiinflammatory pathway control of TNF in endotoxemia. Proceedings of the National Academy of Sciences of the United States of America. 2008;105:11008-11013.
Rosas-Ballina, M. et al. Acetylcholine-synthesizing T cells relay neural signals in a vagus nerve circuit. Science. 2011;334:98-101.
Sadeghi, Z. et al. "Vitamin E administration at the onset of fever prevents renal scarring in acute pyelonephritis." Pediatric Nephrology 23.9 (2008): 1503-1510.

(56) References Cited

OTHER PUBLICATIONS

Sadis, C. et al. Nicotine protects kidney from renal ischemia/reperfusion injury through the cholinergic anti-inflammatory pathway. PloS one. 2007;2:e469.
Saeed, R.W. et al. Cholinergic stimulation blocks endothelial cell activation and leukocyte recruitment during inflammation. The Journal of experimental medicine. 2005;201:1113-1123.
Semercioz, A. et al. Effect of Zinc and Melatonin on Oxidative Stress and Seram Inhibin-B Levels in a Rat Testicular Torsion-Detorsion Model. Biochemical genetics. 2017;55:395-409.
Sessions, A.E. et al. Testicular torsion: direction, degree, duration and disinformation. The Journal of urology. 2003; 169:663-665.
Shapiro, R. & Sarwal, M.M. Pediatric kidney transplantation. Pediatr Clin North Am. Apr. 2010;57(2):393-400, table of contents.
Shytle, R.D. et al. Cholinergic modulation of microglial activation by alpha 7 nicotinic receptors. Journal of neurochemistry. 2004;89:337-343.
Sobouti, B. et al. "The effect of vitamin E or vitamin A on the prevention of renal scarring in children with acute pyelonephritis." Pediatric Nephrology 28.2 (2013): 277-283.
Suzuki, T. et al. Microglial alpha7 nicotinic acetylcholine receptors drive a phospholipase C/IP3 pathway and modulate the cell activation toward a neuroprotective role. Journal of neuroscience research. 2006; 83:1461-1470.
Svensson, M. et al. "Acute pyelonephritis and renal scarring are caused by dysfunctional innate immunity in mCxcr2 heterozygous mice." Kidney international 80.10 (2011): 1064-1072.
Tracey, K.J. "Reflex control of immunity." Nature Reviews Immunology 9.6 (2009): 418-428.

* cited by examiner

FIGURE 2A AND B

METHODS AND COMPOSITIONS FOR THE PREVENTION AND TREATMENT OF ISCHEMIA REPERFUSION INJURY AND INFECTION

CROSS REFERENCE TO RELATED APPLICATIONS

This application is a United States National Phase Patent Application of International Patent Application Number PCT/US2020/059267, filed on Nov. 6, 2020, which claims benefit of U.S. Provisional Application No. 62/931,522, filed Nov. 6, 2019, incorporated herein by reference in its entirety.

BACKGROUND

Ischemia-reperfusion injury (also referred to herein as ischemia perfusion injury) is associated with serious clinical manifestations, including myocardial infarction, acute heart failure, cerebral dysfunction, gastrointestinal dysfunction, systemic inflammatory response syndrome, and multiple organ dysfunction syndrome. Ischemia-reperfusion injury is a critical medical condition that poses an important therapeutic challenge for physicians. Regardless of the affected organ, ischemia results in impaired aerobic metabolism and the production of pro-inflammatory cytokines. When the blood supply is re-established to an ischemic organ, there is a secondary inflammatory response from the innate immune system which results in capillary dysfunction, focal hypoxia and an increased production of reactive oxygen species. Identified as "ischemia reperfusion injury" this secondary inflammatory response results in additional cell death, and permanent end organ dysfunction.

The description of a centrally mediated immunosuppressive cascade has recently revealed a novel mechanism of inhibiting the innate inflammatory response (Rosas 2011). In this pathway, known as the cholinergic anti-inflammatory pathway (CAP), centrally mediated vagal and splenic nerve signaling results in the activation of α7nACh receptors on immune cells including macrophages, B cells, T cells and monocytes, which limits the intracellular response to pro-inflammatory cytokine signaling. The anti-inflammatory effects of α7nAChR signaling have been found to be important in modulating the immune response to inflammatory conditions such as sepsis, peritonitis and pancreatitis (Huston 2006; Wang 2004: van Westerloo 2006). Loss of homeostasis in this system has also been implicated in chronic autoimmune disorders such as inflammatory bowel disease, and rheumatoid arthritis (Andersson 2012).

Cytisine, a nicotine analog which is has been utilized clinically for smoking cessation, also binds to α7nAChR, and has been shown to prevent myeloid lineage cells from mounting an inflammatory response. Gigliotti et al (Gigliotti, Huang et al. 2013) were the first to use Cytisine to activate the CAP in a animal model of warm renal ischemia. They demonstrated that splenic nerve stimulation or administration of cytisine prior to warm renal ischemia reduced the acute immune infiltrate, prevented long term renal fibrosis and preserved long term renal function (Gigliotti 2013). Others have also demonstrated that activation of the CAP with nicotine (an α7nAChR agonist) protects the mouse kidney from IRI after renal artery ligation (Sadis, Teske et al. 2007, Yeboah, Xue et al. 2008). Despite these compelling animal studies, clinical translation has been limited as the peak nicotine concentrations found in smokers and cytisine levels achieved with therapeutic dosing do not activate α7nAChR (Caetano 2016). Occurring after common bacterial infections and routine surgical procedures, ischemia reperfusion injury is pervasive in medicine. Novel therapies are needed to limit the secondary inflammatory response and prevent long term organ dysfunction. What is needed in the art are effective compositions and methods for treating and preventing ischemia reperfusion injury.

SUMMARY

Disclosed herein are methods of treating a subject with ischemia reperfusion injury or at risk of developing ischemia reperfusion injury, the method comprising administering to the subject an agonist of nicotinic cholinergic receptor α7nAchR. The agonist can comprise varenicline or a derivative thereof. The subject can have ischemia, or can be at risk of developing ischemia. For example, the subject can be diagnosed with ischemia prior to administration of the agonist. Alternatively, the subject can be scheduled to undergo a medical procedure or treatment that can cause ischemia, and therefore be at risk of developing ischemia in the future.

In one embodiment, at least a first dose of the agonist is administered in a clinical setting. The subject can be monitored for ischemia reperfusion injury before, after, and/or during administration of the agonist. The subject can be under 18 years old. The subject can have, or can be at risk of developing, testicular torsion. In addition to treatment with an agonist of nicotinic cholinergic receptor α7nAchR, the subject can also treated with one or more additional anti-inflammatory compositions and/or antioxidants.

Also disclosed herein is a method of treating a subject with infection or inflammation, or at risk of developing an infection or inflammation, the method comprising administering to the subject an agonist of nicotinic cholinergic receptor α7nAchR. The agonist can comprise varenicline or a derivative thereof. The subject can be diagnosed with an infection prior to administration of the agonist. At least a first dose of the agonist can be administered in a clinical setting. The subject can be monitored for infection before, after, and/or during administration of the agonist. The subject can also treated with an additional anti-inflammatory composition either before, after, or during administration of the agonist. The subject can also treated with an antibiotic either before, after, or during administration of the agonist. Defined by invasion and growth within the body, an infection can be multifactorial and caused by bacteria, viruses, yeast, fungi or other microorganisms. The infection can begin anywhere in the body and may spread to additional sights, including the bloodstream.

DESCRIPTION OF DRAWINGS

FIG. 1 48 hours following reperfusion of the testis, flow cytometry demonstrates a decreased leukocyte infiltrate in animals treated with varenicline 1 hour after the onset of testicular torsion p≤0.0001).

FIG. 5A: 20× images of trichrome staining. Testes were treated as follows: a) no drug, no torsion; b) no drug, torsion; c) cytisine, no torsion d) cytisine, torsion. B) Image analysis of Masson trichrome stained sections reveals significantly higher percentage of collagen in the untreated animals when compared to those treated with Cytisine (* p<≤0.01) or Varenicline ** p<≤0.0001).

FIG. 6 shows a bar graph representing the results image J analysis of Masson trichrome staining from animals treated with both cytisine and varenicline.

DETAILED DESCRIPTION

Figure 1:
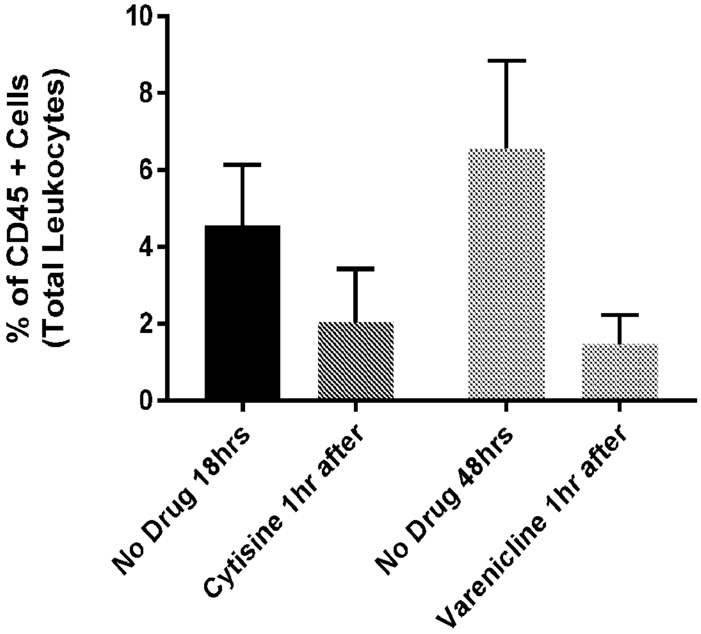

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

In the present invention, "specific" means a condition where one of the molecules involved in specific binding does not show any significant binding to molecules other than a single or a number of binding partner molecules.

The term "subject" is defined herein to include animals such as mammals, including, but not limited to, primates (e.g., humans and nonhuman primates), cows, sheep, goats, horses, dogs, cats, rabbits, rats, mice and the like. In some embodiments, the subject is a human.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

The terms "treat," "treating," "treatment," and grammatical variations thereof as used herein, include partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially. Prophylactic treatments are administered to a subject prior to onset (e.g., before obvious signs of a muscular disease), during early onset (e.g., upon initial signs and symptoms of a muscular disease), or after an established development of muscular disease. Prophylactic administration can occur for several days to years prior to the manifestation of symptoms of a muscular disease.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Pharmacologically active", "functionally active" (or simply "active"), as in a "functionally active" derivative or analog, can refer to a derivative or analog (e.g., a salt, ester, amide, conjugate, metabolite, isomer, fragment, etc.) having the same type of pharmacological activity as the parent compound (e.g., an antibody) and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a chronic muscle disease developed after a physical injury). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

A "decrease" can refer to any change that results in a smaller gene expression, protein expression, amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

"Ischemia" can refer to inadequate blood flow to a tissue or organ, which results in the tissue or organ's inability to meet demands for metabolism. Reperfusion (resumption of blood flow) to the ischemic organ or tissue can lead to the production of excessive amounts of reactive oxygen species (ROS) and reactive nitrogen species (RNS), thus causing oxidative stress which results in a series of events such as alterations in mitochondrial oxidative phosphorylation, depletion of ATP (which also occurs during and as a result of ischemia), an increase in intracellular calcium and activation of protein kinases, phosphatases, proteases, lipases and nucleases leading to loss of cellular function/integrity.

"Ischemia reperfusion injury" (IRI) refers to an injury which occurs as a result of the innate inflammatory response following reperfusion of a previously ischemic organ. By way of additional example and not limitation, such injury also occurs when blood circulation is restarted after being stopped for the transplantation of an organ; after a coronary artery is treated with percutaneous transluminal coronary angioplasty (PTCA), stent, or bypass after myocardial infarction; and after administration of a thrombolytic to a stroke patient. Another example is when blood flow to the heart is temporarily stopped for cardiac surgery, often by the concomitant administration of cardioplegia solutions. Another example is interruption of blood flow to a limb for surgery in a bloodless field by an orthopedic surgeon when a tourniquet is inflated on the limb. Another example is temporary occlusion of renal blood flow to allow for a blood less field during surgery, or temporary renal ischemia due to cardiopulmonary bypass. Focal ischemia also occurs following common bacterial infections such as pyelonephritis, localized abscesses, systemic sepsis. Traumatic injury to extremities and internal organs are also a common cause of focal ischemia. Such an injury can occur in many tissues, such as, but not limited to, kidney, gut, heart, liver, brain, thyroid, skin, intestinal mucosa, auditory system, lung, bladder, ovary, uterus, testicle, adrenal, gallbladder, pancreas, pancreatic islet, stomach, blood vessel, or muscle (e.g., skeletal, smooth, or cardiac muscle) tissue and combinations thereof. In some embodiments, the injury occurs in heart, lung, kidney tissue or combinations thereof.

As used herein, the term "infection" refers to any state in at least one cell of an organism (i.e., a subject) is infected by an infectious agent. As used herein, the term "infectious agent" refers to a foreign biological entity (i.e. a pathogen). For example, infectious agents include, but are not limited to bacteria, viruses, protozoans, and fungi. Infectious diseases are disorders caused by infectious agents. Some infectious agents cause no recognizable symptoms or disease under certain conditions, but have the potential to cause symptoms or disease under changed conditions. The subject methods can be used in the treatment of acute or chronic pathogen infections.

"Inflammation" is the activation of the immune system in response to harmful stimuli, such as, e.g., a pathogen, infection, irritant, or damage to cells. Inflammation can be classified as either acute or chronic. Generally speaking, acute inflammation is mediated by granulocytes, while chronic inflammation is mediated by mononuclear cells such as monocytes and lymphocytes.

A type of systemic inflammation response is referred to as a "cytokine storm," also called hypercytokinemia. A cytokine storm is a physiological reaction in which the innate immune system causes an uncontrolled and excessive release of cytokines. Normally, cytokines are part of the body's immune response to infection, but their sudden release in large quantities can cause multisystem organ failure and death. Cytokine storms can be caused by a number of infectious and non-infectious etiologies, especially viral respiratory infections such as H5N1 influenza, SARS-CoV-1, and SARS-CoV-2 (COVID-19 agent). Other causative agents include the Epstein-Barr virus, cytomegalovirus, and group A streptococcus, and non-infectious conditions such as graft-versus-host disease.

By "at risk of being exposed to ischemia" is meant a subject scheduled for exposure to ischemia in the future or a subject having a chance of being exposed to ischemia inadvertently in the future.

The term "damage resulting from ischemia or hypoxia" as employed herein refers to a condition or conditions directly associated with reduced blood flow or oxygen delivery to tissue, for example due to a clot or obstruction of blood vessels which supply blood to the subject tissue and which result, inter alia, in lowered oxygen transport to such tissue, impaired tissue performance, tissue dysfunction and/or necrosis and/or apoptosis. Alternatively, where blood flow or organ perfusion may be quantitatively adequate, the oxygen carrying capacity of the blood or organ perfusion medium may be reduced, e.g., a in hypoxic environment, such that oxygen supply to the tissue is lowered, and impaired tissue performance, tissue dysfunction, and/or tissue necrosis and/or apoptosis ensues.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon Methods and Compositions Disclosed herein is a method of treating a subject with ischemia perfusion injury or at risk of developing ischemia perfusion injury, and more specifically a method of treating or preventing ischemia reperfusion injury in a person who has, or is at risk of developing, ischemia. The method comprises administering to the subject an agonist of nicotinic cholinergic receptor α7nAchR, thereby preventing an inflammatory response in the ischemic tissue. In the cholinergic anti-inflammatory pathway (CAP), centrally mediated vagal and splenic nerve signaling results in the release of acetylcholine which binds to α7nAChR on macrophages and myeloid lineage cells. α7nAChR signaling then inhibits the NF-KB cascade, preventing a cellular response to pro-inflammatory cytokine signaling. This can prevent or treat ischemia perfusion injury. Therefore, disclosed herein are agonists of α7nAChR which are used to treat or prevent ischemia perfusion injury.

Also disclosed herein is a method of treating a subject with, or at a risk of developing, an infection or inflammation, such as pyelonephritis, by administering to the subject an α7nAChR agonist, such as varenicline.

Disclosed herein is the use of varenicline in the prevention and/or treatment of various disease involving inflammation such as systemic inflammatory response syndrome (SIRS), sepsis, severe sepsis, septic shock, ischemia/reperfusion related injuries such as ischemic heart disease, acute lung injury, pneumonia, acute and chronic graft rejection in transplant patients, graft versus host reactions, but also diseases involving chronic types of inflammation such as renal glomerular diseases such as glomerulonephritis and other entities of renal failure, rheumatoid arthritis and similar auto-immune diseases such as Bechterew's disease, lupus-type diseases, inflammatory bowel disease, or Crohn's disease.

A reduction of an inflammatory response or inflammatory condition associated with one or more tissues, tissue systems, or organs selected from skin, hair follicles, nervous system, auditory system or balance organs, respiratory system, gastroesophogeal tissues, gastrointestinal system, vascular system, liver, gallbladder, lymphatic/immune system, uro-genital system, musculoskeletal system, adipose tissue, mammaries, and endocrine system is disclosed.

As discussed above, disclosed is the treatment of inflammation associated with systemic inflammatory response syndrome (SIRS). Also disclosed is treating inflammation associated with any one or more of granulomatous inflammation, fibrinous inflammation, purulent inflammation, serous inflammation, or ulcerative inflammation. Also disclosed is treating inflammation associated with one or more wounds. The use includes treating inflammation associated with chronic obstructive pulmonary disorder (COPD).

Also disclosed herein is the reduction of an inflammatory condition associated with activity one or more immune cells or vascular cells. In certain embodiments, the immune cell is a granulocyte, lymphocyte, monocyte/macrophage, dendritic cell, or mast cell. In certain embodiments disclosed herein, the granulocyte is a neutrophil, eosinophil, or basophil. In certain embodiments disclosed herein, the lymphocyte is a B-cell, T-cell, natural killer cell. In certain embodiments disclosed herein, the vascular cell is a smooth muscle cell, endothelial cells, or fibroblast. In certain embodiments disclosed herein, the inflammatory condition is a neutrophil-mediated condition, a macrophage-mediated condition, or a lymphocyte-mediated condition.

Specifically, disclosed herein is the α7nAChR agonist varenicline, or 7, 8, 9, 10-tetrahydro-6, 10-methano-6H- pyrazino[2,3-h][3]benzazepine, which is known to bind to neuronal nicotinic acetylcholine specific receptor sites and is useful in modulating cholinergic function. This compound has been used to treat nicotine dependency, addiction and withdrawal; including use in smoking cessation therapy. Varenicline is represented by the following structural formula:

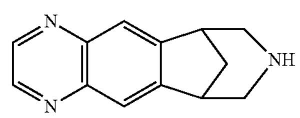 [SMILES: c1cnc2cc3c(cc2n1)C1CNCC3C1]

The first synthesis of varenicline was disclosed in U.S. Pat. No. 6,410,550 (hereinafter referred to as the '550 patent). Varenicline is sold by Pfizer under the brand name CHANTIX™ to help adults quit smoking by blocking α4β2 nicotinic acetylcholine receptor subtypes. It is typically orally administered as tablets containing 0.85 mg or 1.71 mg of varenicline tartrate equivalent to 0.5 mg or 1 mg of varenicline. The '550 patent describes various processes for the preparation of aryl fused azapolycyclic compounds, including varenicline, and their pharmaceutically acceptable salts, combinations with other therapeutic agents, and methods of using such combinations in the treatment of neurological and psychological disorders. Varenicline has been exemplified as a free base and a hydrochloride salt in the '550 patent.

U.S. Pat. No. 6,890,927 (hereinafter referred to as the '927 patent) discloses tartrate salts, including L-tartrate, D-tartrate, D,L-tartrate and meso-tartrate, of varenicline and their polymorphs, processes for their preparation, and pharmaceutical compositions thereof. The '927 patent further discloses various polymorphs of the varenicline L-tartrate salt, including two anhydrous polymorphs (Forms A & B) and a hydrate polymorph (Form C), and characterizes them by powder X-ray diffraction (P-XRD), X-ray crystal structure, solid state 13C NMR spectroscopy, and Differential Scanning Calorimetry (DSC).

Varenicline tartrate, 7, 8, 9, 10-tetrahydro-6, 10-methano-6H-pyrazino[2,3-h][3]benzazepine, (2i?,3/?)-2,3-dihydroxybutanedioate (1:1), has a molecular weight of 361.35 Daltons, and a molecular formula of Ci3Hi3N3.C4H606. Varenicline tartrate is represented by the following structural formula:

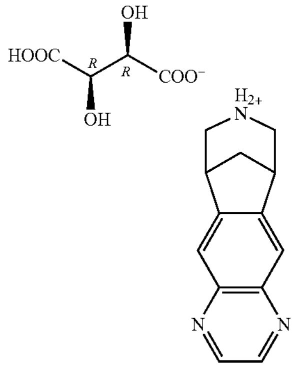

The use of varenicline, as well as its derivatives and salts thereof, are disclosed herein for the treatment of ischemia perfusion injury, as well as for infections and sepsis.

Ischemia Reperfusion Injury

Reperfusion injury, sometimes called ischemia-reperfusion injury (IRI) or reoxygenation injury, is the tissue damage caused when blood supply returns to tissue (re-+perfusion) after a period of ischemia or lack of oxygen (anoxia or hypoxia). The absence of oxygen and nutrients from blood during the ischemic period creates a condition in which the restoration of circulation results in inflammation and oxidative damage through the induction of oxidative stress rather than (or along with) restoration of normal function.

Reperfusion of ischemic tissues is often associated with microvascular injury, particularly due to increased permeability of capillaries and arterioles that lead to an increase of diffusion and fluid filtration across the tissues. Activated endothelial cells produce more reactive oxygen species but less nitric oxide following reperfusion, and the imbalance results in a subsequent inflammatory response. The inflammatory response is partially responsible for the damage of reperfusion injury. White blood cells, carried to the area by the newly returning blood, release a host of inflammatory factors such as interleukins as well as free radicals in response to tissue damage. The restored blood flow reintroduces oxygen within cells that damages cellular proteins, DNA, and the plasma membrane. Damage to the cell's membrane may in turn cause the release of more free radicals. Such reactive species may also act indirectly in redox signaling to turn on apoptosis. White blood cells may also bind to the endothelium of small capillaries, obstructing them and leading to more ischemia.

Reperfusion injury plays a major part in the biochemistry of hypoxic brain injury in stroke. Similar failure processes are involved in brain failure following reversal of cardiac arrest. Repeated bouts of ischemia and reperfusion injury also are thought to be a factor leading to the formation and failure to heal of chronic wounds such as pressure sores and diabetic foot ulcer. Continuous pressure limits blood supply and causes ischemia, and the inflammation occurs during reperfusion. As this process is repeated, it eventually damages tissue enough to cause a wound.

As the timing of the onset of ischemia or ischemia perfusion injury associated with ischemia can't always be predicted, it should be understood the disclosed methods of treating, preventing, reducing, and/or inhibiting ischemia perfusion injury can be used following ischemia, and either prior to or following the onset of ischemia perfusion injury, to treat, prevent, inhibit, and/or reduce ischemia perfusion injury. Where ischemia is due to a medical procedure, such as a transplant, the disclosed methods can be performed any time prior to the onset of ischemia perfusion injury including prior to ischemia. In one aspect, the disclosed methods can be employed 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, 60, 45, 30, 15, 10, 9, 8, 7, 6, 5, 4, 3, 2, or 1 minute prior to the ischemia-causing event; concurrently with the ischemia causing event; or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days after the ischemia causing event, but prior to onset of any symptoms of ischemia perfusion injury.

Diseases caused or aggravated by ischemia or hypoxia, or ischemia/reperfusion for example, cardiovascular diseases [e.g., arteriosclerosis, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.), organ disorders associated with ischemia or ischemic reperfusion [(e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], testicular torsion, cerebrovascular diseases (e.g., ischemic stroke, hemorrhagic stroke, etc.), cerebro ischemic disorders (e.g., disorders associated with cerebral infarction, disorders caused after cerebral apoplexy as sequelae, or cerebral edema.

In some aspects, it is understood and herein contemplated diseases that cause ischemia, and therefore ischemia perfusion injury, can be hereditary. Thus, the disclosed methods of treating, preventing, reducing, and/or inhibiting ischemia perfusion injury can be applied to a subject already afflicted with an underlying disease that can cause ischemia, for example, but prior to the onset of any physical symptoms. In some aspects, the disclosed methods of treating, preventing, reducing, and/or inhibiting ischemia perfusion injury (due to disease, aging, physical injury, or atrophy) can be applied to the subject after onset of physical symptoms. Thus, the methods are not preventing the condition as much as inhibiting progression or reducing the existing ischemia perfusion injury. Accordingly, disclosed herein are treating, preventing, reducing, and/or inhibiting ischemia perfusion injury; wherein the treatment commences after the onset of the condition and after symptoms are observable.

It is understood and herein contemplated that the disclosed treatments can be administered to the subject either before, after, or during an ischemia perfusion injury. Monitoring the subject for ischemia perfusion injury can happen before, during, or after treatment. The disclosed treatments can be given at a rate and for a duration appropriate for treating ischemia reperfusion injury, inflammation, or infection, including, but not limited to the inhibition of the progress of any existing ischemia perfusion injury, inflammation or infection; reduction in any existing ischemia perfusion injury, inflammation or infection; and/or the inhibition, reduction, and/or prevention of any future ischemia perfusion injury, inflammation, or infection.

It is important to note that the subject can be diagnosed with ischemia, inflammation, or infection (such as sepsis) before treatment with an agonist of 7nAChR, such as varenicline or a derivative thereof. Specifically, the subject can be diagnosed by a physician as being in need of an agonist of 7nAChR to treat or prevent ischemia reperfusion injury, or to reduce systemic inflammation. The subject may or may not be a smoker. The subject may or may not be enrolled in a clinically prescribed smoking cessation program. In one example, the subject is given an agonist of 7nAChR in an amount or for a period of time which would not be consistent with a smoking cessation program.

Typically, for smoking cessation, a regimen which slowly increases the dose and frequency of varenicline administration is prescribed in the week prior to a scheduled quit date. Treatment with a 1 mg dose, is then continued twice daily for 12 weeks. For treatment of ischemia reperfusion injury, or systemic inflammation, a dose is administered at the time that ischemia, inflammation, or infection is diagnosed, or immediately prior to a scheduled procedure which will induce ischemia, inflammation, or infection. Varenicline administration is then continued after the surgery or diagnosis of ischemia. In one example, the subject may be given 10 or less doses of an agonist of 7nAChR such as varenicline. This is in contrast to a smoking cessation program.

When an agonist of 7nAChR is given to treat or prevent ischemic reperfusion injury, inflammation, or infection (such as sepsis), it can be given at an initial dose of 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0 mg or more, or any amount in between these amounts. This dose may be the only dose given, or the subject may be given one or more additional doses following the initial treatment. For example, the subject may be given the initial dose of the agonist of 7nAChR, then may be given one or more follow-up doses within 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96 hours or more or the initial dose. Subsequent doses after the initial dose may be given at the same amount as the initial dose, or a higher or lower dose may be given in subsequent doses. The subsequent dose(s) can be given at the same amounts specified above for the initial dose, or can be above or below these amounts. The subject may be re-evaluated for progress during the course of treatment, and the dosage varied according to the individual needs of the subject.

Thus, in one aspect, disclosed herein are methods of treating, preventing, reducing, and/or inhibiting ischemia perfusion injury, inflammation, or infection, wherein the treatment is applied at a rate of 1, 2, 3, 4, 5, 6, 7, 8, 9, 10, 11, 12 or more times per day, 1, 2, 3, 4, 5, 6, or 7 times per week, 1, 2, 3, 4, 5, 6, 7, 8, 9, 10, 11, 12, 13, 14, 15, 16 or more times per month, 1, 2, 3, 4, 5, 6, 7, 8, 9, 10, 11, 12, 13, 14, 15, 16, 17, 18, 19, 20, 21, 22, 23, 24 or more times per year. In some aspect, the treatment can be applied a single time, twice, 3, 4, 5, 6, 7, 8, 9, 10, 11, 12, 13, 14, 15, 16, 17 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more times to the subject of a period of 1, 2, 3, 4, 5, 6, 7, 8, 9, 10, 11, 12, 13, 14, 21, 30, 31, 36, 45, 60, 75, 90 days, 3, 4, 5, 6, 7, 8, 9, 10, 11, 12, 16, 18, 24 months, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more years. In one aspect, the treatment is administered at the appropriate rate as determined by a physician for the remaining life of the subject.

Infection and Sepsis

It will be appreciated that in this specification the subject in need thereof may have been infected or suffering from an infection or at risk of developing an infection and the injury to the cells, tissues and/or organs is reduced or minimized by the administration of the composition disclosed herein. Severe infection in a subject can lead to sepsis.

Sepsis is a severe complication of critically ill patients that is characterized by the systemic inflammatory response syndrome (SIRS) and the early release of pro-inflammatory cytokines, such as tumor necrosis factor (TNF-alpha), IL-1 and IL-6, and together these cytokines contribute to the development of multiple organ dysfunction/failure syndrome (MODS). Initially, in response to infection or injury cytokines are produced and released by activated neutrophils, monocytes and macrophages. Normally these proinflammatory cytokines help to fight infection, remove dead cells and promote tissue repair, however, in conditions such as sepsis, the process becomes massively amplified. The so-called systemic inflammatory response, in turn, mediates its deleterious effects by inducing tissue hypoxia, and cellular injury, either through tissue necrosis or through the induction of programmed cell death or apoptosis.

Sepsis always leads to a derangement to the coagulation system, ranging from mild alterations up to severe disseminated intravascular coagulation (DIC) (hypercoagulopathy). Septic patients with severe DIC have microvascular fibrin deposition, which can lead to MODS and death. Alternatively, in sepsis severe bleeding might be the leading symptom (hypocoagulopathy), or even coexisting bleeding and thrombosis. The deranged coagulation, particularly DIC, is an important and independent predictor of mortality in patients with severe sepsis.

Sepsis affects the central nervous system indicated from reduced heart rate variability and impaired baroreflex and chemoreflex sensitivities. During human infection there is a decreased beat-to-beat or pulse-to-pulse variation ("variability") of heart rate and blood pressure oscillations, respectively suggesting an uncoupling of the autonomic and cardiovascular systems on a physiological level. Body temperature dysregulation is also believed to be an indicator of CNS impairment. CNS impairment (involving the vagus nerve) is associated with the development of the state of immunosuppression causing stimulation of nicotinic acetyl choline receptors on tissue macrophages with resultant inhibition of macrophage production of cytokines.

Infection is common following trauma. Approximately 6% of all trauma patients will develop an infectious complication, a risk related to the degree of injury. Infections arise from: i) penetrating and/or ii) non-penetrating wounds. The development of an infectious complication marks the onset of a "second hit" with further disruptions in the inflammatory response. Multiple factors increase the risk of infection in trauma such as imbalances to the immune and inflammatory systems (immune-inflammatory system), breaks in the skin surface and mucosal surfaces, which become colonized with organisms after trauma.

Infection is common following burns and sepsis is the leading cause of mortality with debilitating scar formation. Surgical intervention is required to reestablish normal barrier functions and prevent infectious sequelae. Burn trauma induces localized tissue coagulation and microvascular reactions in the underlying dermis that can lead to injury extension.

Infectious complications are frequently reported in critically ill patients (e.g. type 2 diabetes mellitus, chronic obstructive pulmonary disease, chronic heart failure and chronic renal disease). Infections are common after traumatic brain injury, heart attack, cardiac arrest, hemorrhagic shock, non-hemorrhagic shock, surgery and radiation therapy for cancers. Pneumonia occurs in 5-22% and is the most common cause of death in stroke patients. Patients who receive hemodialysis are at a significant risk of developing infections, a leading cause of hospitalization and death in this patient.

If infection occurs after surgery it increases the risk of death and morbidity. Infection increases the risk of adhesions. Adhesions develop as the body attempts to repair itself from infection, surgery, injury (trauma) and radiation. Up to 93% of people who have abdominal surgery go on to develop adhesions.

A urinary tract infection (UTI) is an infection that begins in the urinary system. Serious consequences can occur if the infection spreads to the kidneys. Women are most at risk of developing a UTI. In fact, half of all women will develop a UTI during their lifetimes, and many will experience more than one. When treated promptly and properly, UTIs rarely lead to complications. But left untreated, a urinary tract infection can become something more serious than a set of uncomfortable symptoms. Untreated UTIs can lead to acute or chronic kidney infections (pyelonephritis), which could permanently damage kidneys. Young children and older adults are at the greatest risk of kidney damage due to UTIs because their symptoms are often overlooked or mistaken for other conditions. Women who have UTIs while pregnant may also have an increased risk of delivering low birth weight or premature infants.

As the timing of the onset of infection or sepsis can't always be predicted, it should be understood the disclosed methods of treating, preventing, reducing, and/or inhibiting infection, and either prior to or following the onset of infection, to treat, prevent, inhibit, and/or reduce infection. Where infection or sepsis is due to a medical procedure, such as a transplant or surgery, the disclosed methods can be performed any time prior to the onset of infection or sepsis. In one aspect, the disclosed methods can be employed 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, 60, 45, 30, 15, 10, 9, 8, 7, 6, 5, 4, 3, 2, or 1 minute prior to the potentially infection-causing event; concurrently with the infection causing event; or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days after the infection causing event, but prior to onset of any symptoms of infection or sepsis.

It is understood and herein contemplated that the disclosed treatments can be administered to the subject either before or during infection or sepsis. Monitoring the subject for infection can happen before, during, or after treatment. The disclosed treatments can be given at a rate and for a duration appropriate for treating infection, including, but not limited to the inhibition of the progress of any existing infection; reduction in any existing infection; and/or the inhibition, reduction, and/or prevention of any future infection. Thus, in one aspect, disclosed herein are methods of treating, preventing, reducing, and/or inhibiting infection or sepsis, wherein the treatment is applied at a rate of 1, 2, 3, 4, 5, 6, 7, 8, 9, 10, 11, 12 or more times per day, 1, 2, 3, 4, 5, 6, or 7 times per week, 1, 2, 3, 4, 5, 6, 7, 8, 9, 10, 11, 12, 13, 14, 15, 16 or more times per month, 1, 2, 3, 4, 5, 6, 7, 8, 9, 10, 11, 12, 13, 14, 15, 16, 17, 18, 19, 20, 21, 22, 23, 24 or more times per year. In some aspect, the treatment can be applied a single time, twice, 3, 4, 5, 6, 7, 8, 9, 10, 11, 12, 13, 14, 15, 16, 17 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more times to the subject of a period of 1, 2, 3, 4, 5, 6, 7, 8, 9, 10, 11, 12, 13, 14, 21, 30, 31, 36, 45, 60, 75, 90 days, 3, 4, 5, 6, 7, 8, 9, 10, 11, 12, 16, 18, 24 months, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more years. In one aspect, the treatment is administered at the appropriate rate as determined by a physician for the remaining life of the subject.

It is important to note that the subject can be diagnosed with an infection or with sepsis before treatment with an agonist of 7nAChR, such as varenicline or a derivative thereof. Specifically, the subject can be diagnosed by a physician as being in need of an agonist of α7nAChR to treat or infection or sepsis specifically. The subject may or may not be a smoker. In one example, the subject is given an agonist of 7nAChR in an amount or for a period of time which would not be consistent with a smoking cessation program.

General Dosing and Administration

In some embodiments, the dosing frequency for the therapeutic agent includes, but is not limited to, at least once a day, twice a day, three times a day, or four times a day. In some embodiments, the interval between each administration is less than about 48 hours, 36 hours, 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is less than about 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is constant. Administration can also be continuous and adjusted to maintaining a level of the compound within any desired and specified range.

The agonists described herein can be given to those under 18 years of age, so those who would not be using Varenicline to stop smoking. It can be given in a clinical setting, such as in a hospital or physician's office. This can occur the first time it's given, or every time it's given.

The administration of the composition can be for a shortened period of time, which is referred to herein as an "acute dosage." This is in contrast to how, for example, the composition Varenicline would be given for a smoking cessation program, which would be a "chronic dosage." For an acute dosage, Varenicline may be administered less than 25, 20, 15, 10, 9, 8, 7, 6, 5, 4, 3, 2 times. In other words, Varenicline may be administered in only a few doses to be effective. On the contrary, when Varenicline is given in conjunction with a smoking cessation program, it might be given for a month or longer, or up to about three years or longer. For example, the dosing regimen can be extended over a period of any of about 2, 3, 4, 5, 6, 7, 8, 9, 10, 11, 12, 18, 24, 30, and 36 months.

It is understood and herein contemplated that the disclosed methods of treating, preventing, reducing, and/or inhibiting ischemia perfusion injury can be administered to any subject with, or the potential for developing ischemia perfusion injury, including, but not limited to humans, dogs, cats, horses, cows, mice, rats, pigs, sheep, and non-human primates.

EXAMPLES

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. While the invention has been described with reference to particular embodiments and implementations, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

Example 1: Activation of Central Immunosuppressive Cascade Prevents Testicular Ischemia Reperfusion Injury

Summary

Background

Affecting up to 1 in 4800 adolescent males, torsion of the spermatic cord results in acute testicular ischemia which requires emergent surgical intervention to re-perfuse the testis. After reperfusion of the testis, an immune mediated inflammatory response results in the production of reactive oxygen species, local capillary dysfunction and further tissue injury. The impact of this ischemia reperfusion injury (IRI) is highlighted by the common finding of long-term testicular atrophy despite rapid surgical intervention and limiting ischemia times to under 4 hours. A novel central immunosuppressive cascade has been identified which activates α7nAch receptors and limits the intracellular response to NFLβ signaling. Treatment with the α7nAchR agonist, cytisine reduces ischemia reperfusion injury, preserving renal function and limiting long term renal fibrosis following warm renal ischemia. It was hypothesized that administration of the α7nAchR agonists cytisine and varenicline would decrease IRI and prevent testicular atrophy following testicular torsion.

Methods:

Unilateral testicular torsion was induced in mature male CD1 mice by rotating the right testicle 720 degrees for 2 hours. Treatment with cytisine or varenicline was initiated one hour prior or one hour after the creation of testicular torsion. Testes were harvested 18 hours and 30 days following reperfusion. The acute inflammatory response was quantified with FACS analysis, measurement of, reduced glutathione levels and quantification of the expression of IRI markers. Long term (30 day) outcomes were assessed by histologic evaluation, quantification of the expression of pro-fibrotic genes and measurement of testicular weight.

Result:

Acutely following testicular torsion, the systemic administration of cytisine or varenicline significantly decreased the intravesicular leukocyte infiltrate, and the expression of ischemia re-perfusion injury markers. Treatment with cytisine or varenicline also prevented long term testicular atrophy, decreased the expression of pro-fibrotic genes and histologic evidence of testicular fibrosis.

Discussion:

Activation of a central immunosuppressive cascade with the α7nAchR agonists cytisine or varenicline limits ischemia reperfusion injury and limits long term testicular atrophy and fibrosis in a murine model of testicular torsion.

Introduction

Testicular ischemia due to torsion of the spermatic cord affects approximately 1 in 4800 adolescent males and is one of the most common surgical emergencies encountered in pediatric urology (Zhao 2011). Acutely, testicular ischemia leads to the production of inflammatory cytokines and cell death due impaired aerobic metabolism. After reperfusion of the testis, there is a robust immune mediated inflammatory response which results in further tissue injury due to the production of reactive oxygen species and local capillary dysfunction. Rapid diagnosis and surgical detorsion of the effected testis are the mainstay of current therapy, however, these alone are inadequate as long term testicular atrophy occurs in 40% of patients despite reperfusion of the testis within 4 hours (Sessions 2003; Tryfonas 1994; Visser 2003). Loss of germ cells and subsequent fibrosis can impact future fertility potential with reported oligospermia in 30% of men with a history of unilateral testicular torsion (Visser 2003; Anderson 1992; Krarup 1978). Additional treatments to mitigate testicular damage caused by ischemia reperfusion injury are needed.

Acutely, testicular ischemia leads to the production of inflammatory cytokines and cell death due to impaired aerobic metabolism. After reperfusion of the testis, there is a robust innate inflammatory response, which results in further tissue injury due to the production of reactive oxygen species (ROS) and local capillary dysfunction. Blunting the innate inflammatory response with the antioxidants Taurine (Wei 2007), Rutin (Wei 2010), Probucol (Wei 2017), Apocynin (Ozbek 2014), Omega-3 polyunsaturated fatty acids (Qi 2017) and Zinc (Semercioz 2017) have been shown to acutely decrease testicular myeloperoxidase activity and preserve long term spermatogenesis in animal models of testicular torsion. While the results of these studies are encouraging, the translation to human subjects is limited as the described anti-inflammatory compounds are either non-FDA approved or require administration prior to the onset of testicular torsion. The anti-inflammatory medications Etoricoxib (Yapanoglu 2017) and Rapamycin (Ghasmenejad-Berenji 2017) decrease apoptosis and oxidative stress when administered prior to testicular reperfusion, however no long term results have been reported to date. Targeted inhibition of the inflammatory cascade with interfering micro-RNAs has also been found to acutely limit Sertoli cell apoptosis after testicular torsion (Ning 2017), but requires direct delivery of the micro-RNA to the testis. Lastly, E-selectin-deficient mice which are unable to recruit neutrophils to the site of injury displayed decreased myeloperoxidase activity compared to wild-type mice after torsion (Lysiak 2001). Together, these studies demonstrate a key role for the innate immune response and immune cell recruitment in the development of IRI and production of ROS after torsion. Clinically, an FDA approved anti-inflammatory medication which can be easily administered when a patient presents with testicular torsion, can serve as a novel adjunct to surgical management.

FDA approved as a α4β2nAChR agonist and smoking cessation aid, Varenicline (Chantix®) is also α7nAChR agonist at concentrations found with therapeutic dosing in humans (Campling 2013). Given its pharmokinetic and side effect profile, Varenicline offers a novel, FDA approved mechanism of manipulating the cholinergic anti-inflammatory pathway. Varenicline administration can prevent testicular atrophy and fibrosis in a murine model of testicular torsion.

Methods

Animals and Torsion Model

Adult male CD1 mice (8 weeks old) were purchased from Charles River Laboratories (Wilmington, MA) or Envigo (United Kingdom). Mice were housed in 12-hour dark light cycles with free access to standard mouse chow and water. The animal protocol was approved by the Institutional Animal Care and Use Committee at our Institution.

Mice underwent testicular torsion as previously described (Lysiak 2001). Briefly, mice were anesthetized with isoflurane over a heating pad. The right testis was delivered through a low scrotal incision and rotated counterclockwise 720 degrees to induce ischemia for 2 hours. This model has been shown to disrupt seminiferous epithelium and permanently disrupt spermatogenesis (Lsyiak 2001) Following detorsion, the testis was gently replaced within the right hemiscrotum and skin was sutured using #5-0 chromic in a mattress suture fashion. All animals were injected with long-acting buprenorphine (0.1 mg/kg) for long-term pain control prior to being recovered from anesthesia. Mice were euthanized either 18 hours or 30 days following torsion. Mice kept for 30 days after surgery were weighed on a weekly basis.

Cytisine (Sigma-Aldrich, St. Louis, MO) was administered intraperitoneally at a dose of 0.1 μg/gram either 1 hour before torsion or 1 hour after torsion (1 hour prior to detorsion). Varenicline (1 grm/kg) was administered as an intraperitoneal injection one hour after the onset of torsion and then continued every 12 hours for a total of 4 doses.

Flow Cytometry

Eighteen hours after reperfusion of the testis in the cytisine group and 48 hours after reperfusion in the varenicline group, bilateral testes were harvested, homogenized and digested with digestion solution containing 0.5% FBS, 20 mM HEPES, RPMI Medium, 0.057 U/ml DNase I, 1 mg/ml collagenase b. Cells were washed, counted with a hemocytometer and 1 million then diluted to 1 million cells per mL. CD45+ was identified using APC-labeled anti-CD45 (BioLegend, San Diego, CA) and live cells were tagged with Live/dead fixable yellow dead cell stain kit (Invitrogen, Carlsbad, CA). For each sample 300,000 live cells were counted using BD FACSCalibur (BD Biosciences, San Jose, CA) and analyzed with FlowJo 9.0 software (TreeStar, Ashland, OR).

Real Time PCR

RNA was isolated from testis tissue using RNEasy mini kit (Qiagen, Hilden, Germany) using the manufacturer's protocol. RNA concentration was measured with Nanodrop 8000 (Thermo Scientific, Waltham, MA). cDNA was synthesized using Superscript First-Strand Synthesis system for RT-PCR (Invitrogen, Carlsbad, CA) on a GeneAmp PCR System 9700 (Applied Biosystems, Foster City, CA) Real-Real-time PCR was performed using QuantStudio 7 Flex (Applied Biosystems, Foster City, CA). Software Quantstudio Real-Time PCR Software (Thermo Fisher Scientific, Waltham, MA). TaqMan Gene Expression Assays (Applied Biosystems, Foster City, CA). Standard TaqMan primers were used for Col1, Col3, Vim, SMA.

Glutathione Reductase Assay

Tissues were harvested and stored at −80° C. until use. Glutathione reductase activity was measured by use of glutathione reductase assay Kit (Sigma-Aldrich, St. Louis, MO). Testis tissue was homogenized in 5% sulfosalicylic Acid (SSA) solution. Samples were then centrifuged and supernatant was reserved. Supernatants were added to a reaction mixture containing 95 mM potassium phosphate buffer, pH 7.0, 0.95 mM EDTA, 0.038 mg/mL NADPH, 0.031 mg/mL DTNB, 0.115 units/mL glutathione reductase, and 0.24% SSA. Absorbance at 412 nm was recorded. Glutathione results were expressed as nm GSH per mL sample.

Histological Analysis

Testis tissue was harvested and stored in 70% ethanol. Fixation, embedding, sectioning, and staining were performed by the research pathology core at George Washington University. Sections were cut at a thickness of 5 μM. Tissues were stained for H&E or Masson trichrome. Photographs were scanned at 20× resolution with Olympus VS120 virtual slide microscope system. TIF images were analyzed with ImageJ Fiji software as previously described (Caetano, Fronza et al. 2016). The color deconvolution plugin was used to perform ImageJ analysis on an area measuring 3000 square pixels. Automatic thresholding was performed. The amount of collagen in each area is expressed as the percentage of blue pixels in the image area taken as an average of 3 non-overlapping measurements.

Statistical Analysis

One-way ANOVA or Student's t-test were utilized as appropriate. Post hoc testing was performed with Bonferroni test. A p-value less than 0.05 was considered statistically significant. Results Effect of CAP Activation on Acute Immune Cell Infiltrate Production of pro-inflammatory cytokines by ischemic tissues results in recruitment of neutrophils and macrophages to the testis following reperfusion. In order to assess the infiltration of immune cells following torsion, flow cytometry was performed to quantify the presence of CD45+ cells. In our model, the right testis was torsed and the left testis was not, allowing for comparison of experimental and control tissue from the same animal. Eighteen hours after reperfusion, the mice that underwent torsion and received cytisine pretreatment had significantly decreased CD45+ immune cells in the torsed testis when compared to mice who did not receive cytisine (FIG. 1) ($P<0.0001$). Treatment with varenicline 1 hour after the creation of testicular torsion similarly resulted in an acute reduction in the acute immune cell infiltrate 48 hours following reperfusion (FIG. 1) ($P\leq 0.0001$).

Effect of CAP Activation on Oxidative Stress

Figure 2:
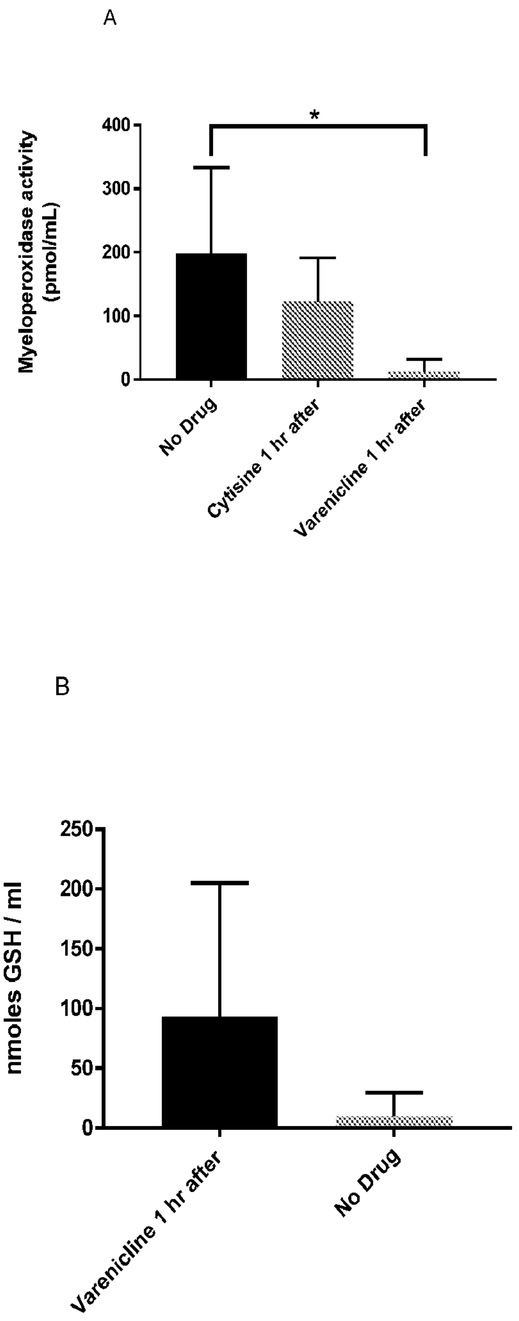
FIG. 2A-B shows oxidative stress caused by testicular torsion is reversed by activation of cholinergic anti-inflammatory pathway. A) Myeloperoxidase activity is significantly decreased following varenicline administration (*p≤0.0013) B) Varenicline administration preserved reduced glutathione levels 48 hours following testicular reperfusion p≤0.0742).

Following an ischemic event, the initial inflammatory response is characterized by an increase in oxidative stress and production of reactive oxygen species. In order to determine the effect of cytisine treatment on the level of reactive oxygen species (ROS) following testicular torsion, testicular levels of myeloperoxidase (MPO), a marker of neutrophil activation, and reduced glutathione (GSH) levels (an indirect measure of oxidative stress within the testis) were measured. In animals treated with varenicline there were decreased levels of MPO activity (FIG. 2*a*, $P\leq 0.0013$) and increased levels of reduced glutathione (GSH) (FIG. 2*b*, $P\leq 0.0742$) when compared to untreated controls.

Figure 3:
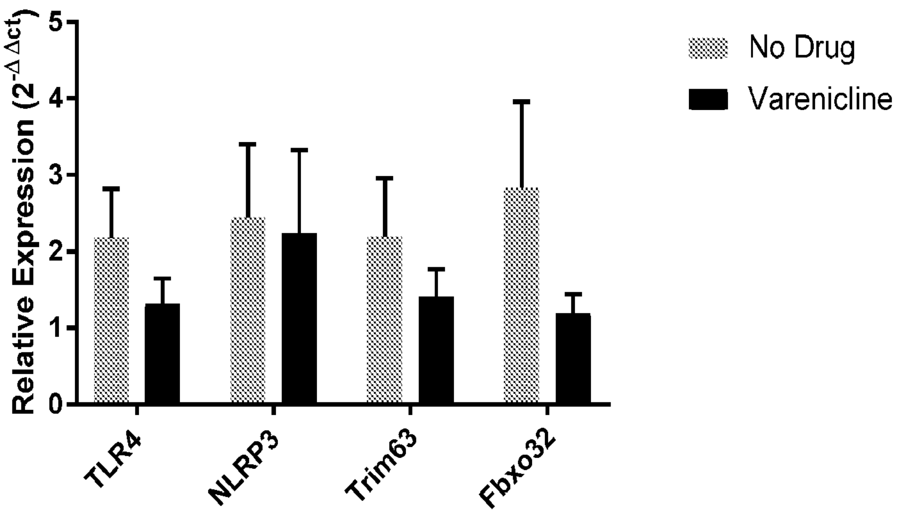
FIG. 3 shows RT-PCR analysis of NF-KB target genes 18 hours following testicular torsion. Treatment with varenicline decreased the expression of TLR4 (p<≤0.0103), NLRP3 (p<≤0.054), Trim63 (p<≤0.053), Fbxo32 (p<≤0.0001 03)

Activation of the CAP Acutely Decreases Expression of Downstream NFKB Targets Following Testicular Torsion NFKB signaling results in the upregulation of several downstream targets, which propagate the inflammatory cascade. To determine if varenicline administration reduced activation of the NFKB axis, quantitative PCR of established downstream NFKB targets was performed. The administration of varenicline significantly decreased the expression of TLR4 ($p<0.01$), NLRP3 ($p<0.05$), Trim63 ($p\leq 0.034$), and Fbxo32 ($p<0.0001$) (FIG. 3).

CAP Activation Reduces Long Term Testicular Atrophy and Fibrosis Following Testicular Torsion Long-term outcomes were assessed 30 days following testicular reperfusion. The degree of testicular atrophy was determined by comparing the weight of the torsed testis to the contralateral control testis 30 days after reperfusion. Pretreatment with cytisine an hour prior to torsion resulted in significantly less testicular atrophy when compared to untreated animals. (FIG. 3; $p<0.05$). This effect persisted when cytisine or varenicline was administered an hour after the onset of torsion. ($p<0.01$).

Figure 4:
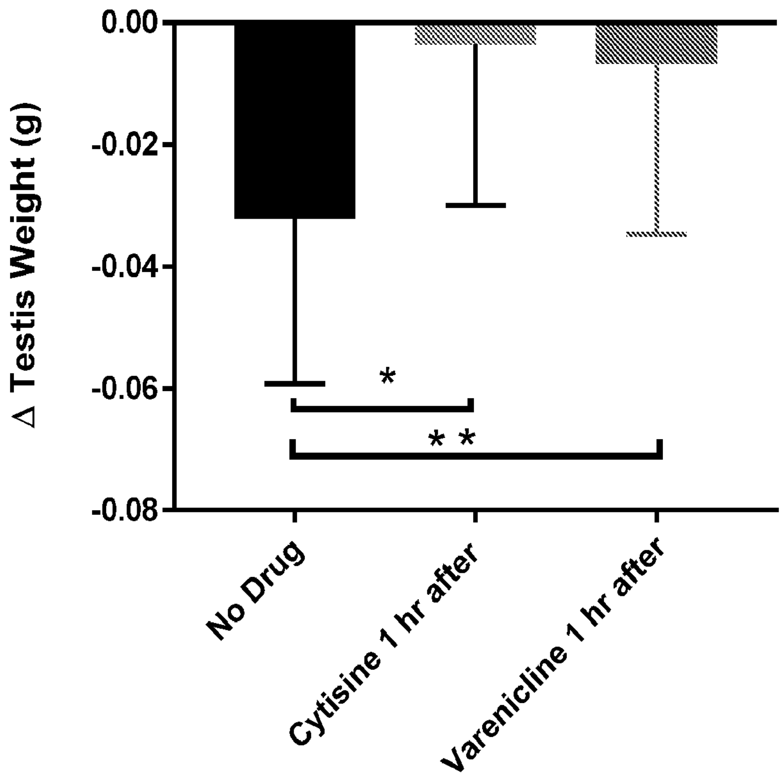
FIG. 4 shows testis weights which were measured 30 days following torsion and compared to the contralateral testis. Cytisine or varenicline administration limited testicular atrophy compared to control mice. Weights are expressed as percent change compared to contralateral control testis.

Treatment with cytisine or varenicline also reduced the expression of pro-fibrotic markers collagen 1 (Col1), collagen 3 (Col3), vimentin (Vim), and smooth muscle actin (SMA) when compared to untreated animals (FIG. 4). Administration of cytisine or varenicline one hour after the onset of torsion similarly limited long term testicular atrophy (FIG. 4; $p<0.05$).

Testis harvested at 30 days underwent histologic analysis and trichrome staining in order to quantify collagen deposition as a marker of fibrosis. Testis from the untreated group had significantly higher collagen content when compared to animals treated with cytisine (FIG. 4; $p<0.01$) or varenicline (FIG. 5; $p<0.0001$).

Quantitative PCR for pro-fibrotic markers collagen 1 (Col1), collagen 3 (Col3), vimentin (Vim), and smooth muscle actin (SMA) was performed on testis tissue harvested at 30 days. The administration of Varenicline or Cytisine significantly decreased the relative expression of pro-fibrotic gene markers collagen 3 (Col3) (Varenicline $p<0.05$; Cytisine $p<0.001$), collagen 1 (Col1) (Varenicline $p<0.001$; Cytisine $p<0.001$) smooth muscle actin (Sma) (Varenicline $p<0.05$; Cytisine $p<0.001$) and vimentin (Vim) (Varenicline $p=0.09$; Cytisine $p<0.01$)/

Discussion

Torsion of the spermatic cord is a common pediatric urologic emergency which often results in long term testicular atrophy. While protocols have been developed to streamline surgical intervention, there is currently no available therapy to mitigate injury due to the post reperfusion inflammatory response. Disclosed herein is the administration of cytisine or the FDA approved α7nAChR agonist varenicline to reduce ischemia reperfusion injury and prevent long term testicular atrophy in a murine model of testicular torsion.

Investigators have previously studied the ability of antioxidants (Anderson 1986; Anderson 1992; Krarup 1978; Wei 2011; Wei 2007; Wei 2017; Ozbek 2015; Qi 2017; and Semercioz 2017), anti-inflammatory medications (Yapanoglu 2017; Ghasemnejad 2017) and targeted genetic approaches (Ning 2017) to reduce the innate immune response following an ischemic event. Although these prior studies have demonstrated the ability to decrease the innate immune response, translation of the findings to a clinical setting has been limited as the investigated compounds are not FDA approved, associated with potential significant side effects, or have only been investigated when administered prior to the ischemic event.

The description of the cholinergic anti-inflammatory pathway has recently revealed a novel mechanism of inhibiting the innate inflammatory response (Rosas-Ballina 2011). In this pathway, activation of α7nAChR inhibits intracellular phosphorylation of MAPK1430/MAPK331, IκB32 and activates Jak2-STAT3 signaling (de Jonge 2005), preventing propagation of the NF-κB cascade. By inhibiting NF-κB signaling, α7nAChR signaling prevents a cellular response to pro-inflammatory cytokine signaling, reducing the production of inflammatory cytokines such as TNF (Parrish 2008), HMGB120, CD-14 and TLR4 (Rosas-Ballina 2008). Using the nicotine analog and α7nAChR agonist Cytisine, Gigliotti et al (2013) reported that pre-treatment with cytisine reduced ischemia reperfusion injury following warm renal ischemia. In clinical practice, testicular atrophy can occur following any length of ischemia, however the incidence of long-term atrophy and testicular loss rises exponentially after 6 hours of warm ischemia. As patient's do not present for medical treatment until they experience pain due to testicular ischemia, the opportunity to manipulate the CAP would present after the onset of testicular ischemia. The 720-degrees of torsion and 2 hours of warm testicular ischemia utilized in the model resulted in testicular atrophy and fibrosis 30 days following reperfusion of the testis (Lysiak 2001). One hour following the creation of testicular torsion was selected as a time point of medication administration which would closely mirror clinical practice.

Figure 5A:
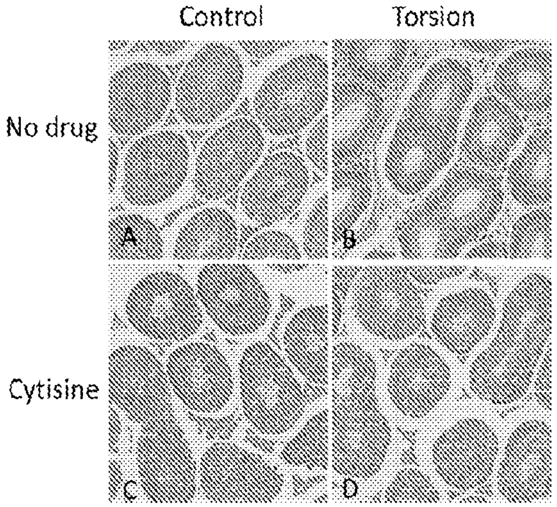
FIG. 5A-B shows trichrome staining and quantification of collagen deposition within testis 30 days following torsion.
Figure 5B:
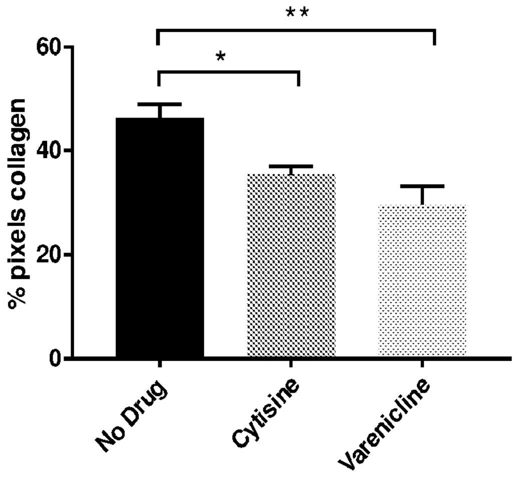
Figure 6:
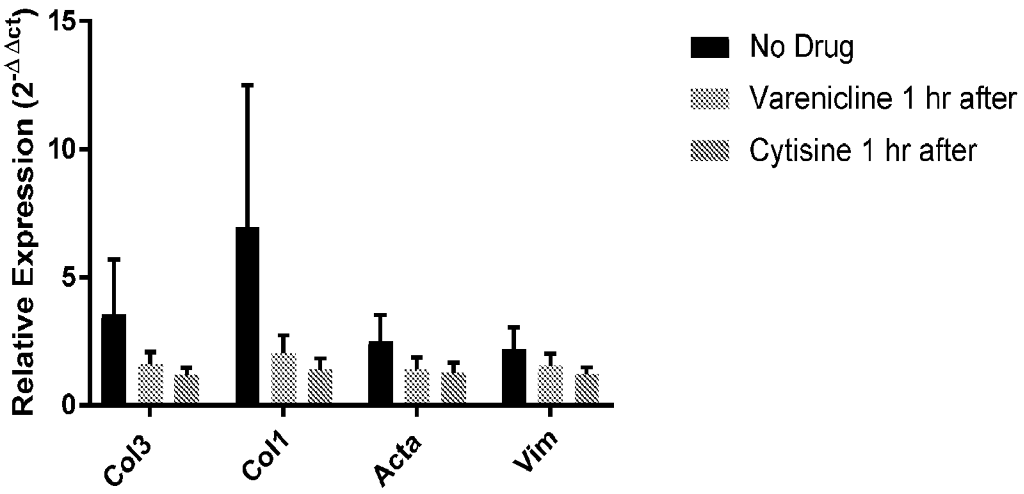
FIG. 6 shows RT-PCR analysis of pro-fibrotic markers 30 days following testicular torsion. The administration of varenicline or cytisine significantly decreased the relative expression of pro-fibrotic gene markers collagen 3 (Col3) (p<0.05, p<0.001), collagen 1 (Col1) (p<0.01, p<0.001) smooth muscle actin (Sma) (p<0.05, p<0.001) and vimentin (Vim) (p<0.05, p<0.01).
Figure 7:
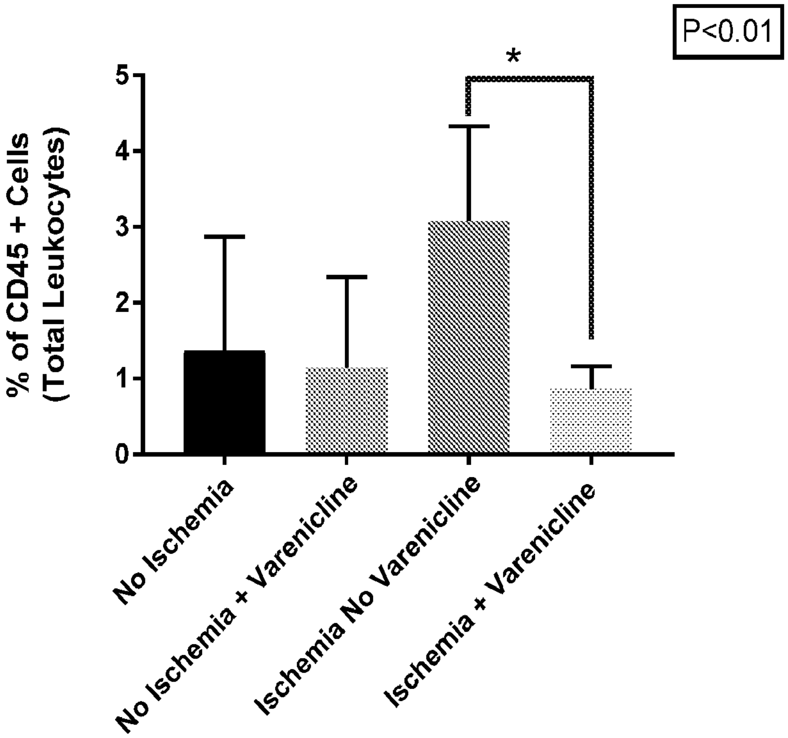
FIG. 7 flow cytometry analysis 24 hours after warm ischemia of the hindlimb demonstrates decreased infiltration of leukocytes in animals treated with varenicline (n=4) compared to untreated controls (n=4) P≤0.01.
Figure 8:
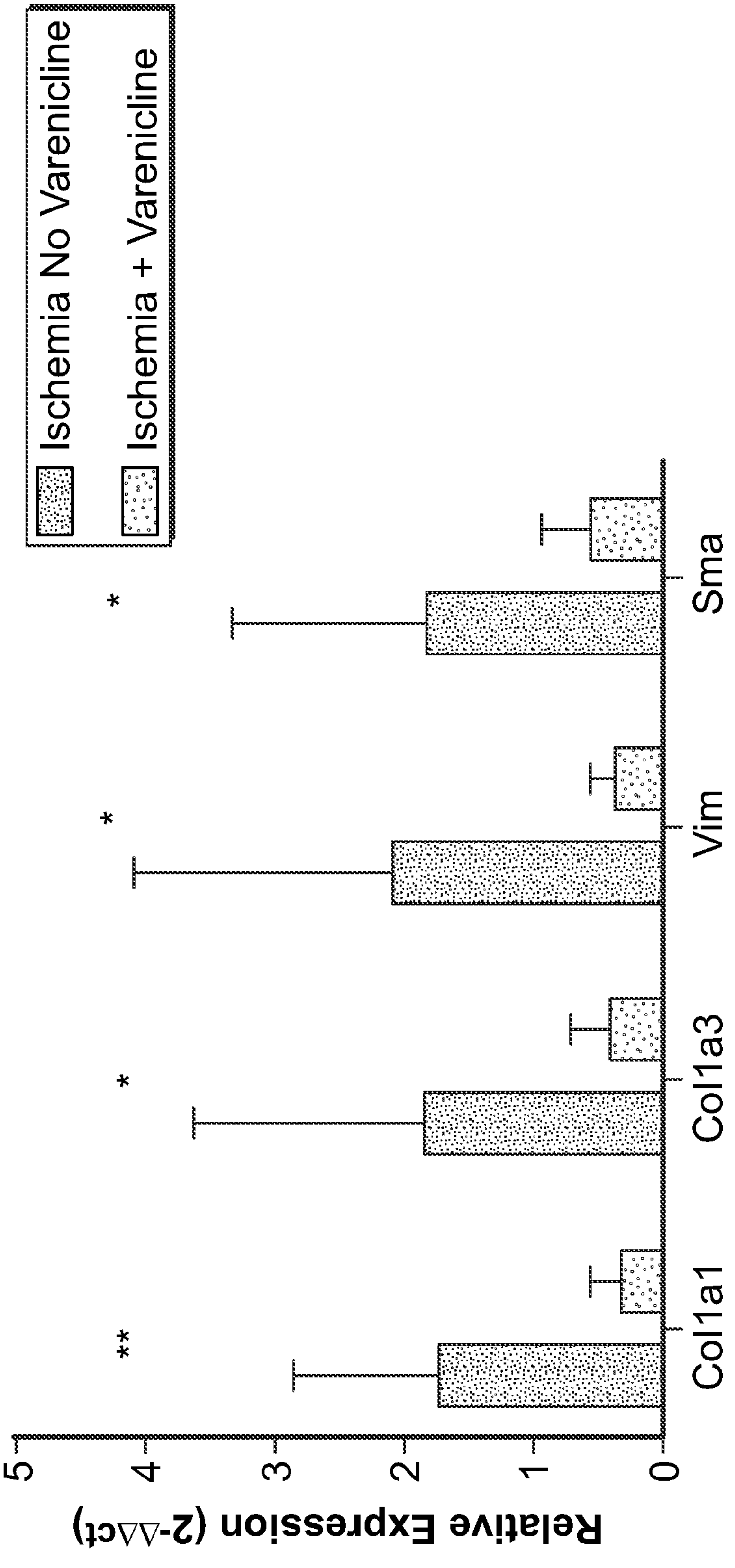
FIG. 8 shows quantitative PCR performed 7 days after reperfusion of the limb which demonstrates decreased expression of pro-fibrotic genes in animals treated with varenicline (N=8) when compared to untreated controls (N=8).
Figure 9:
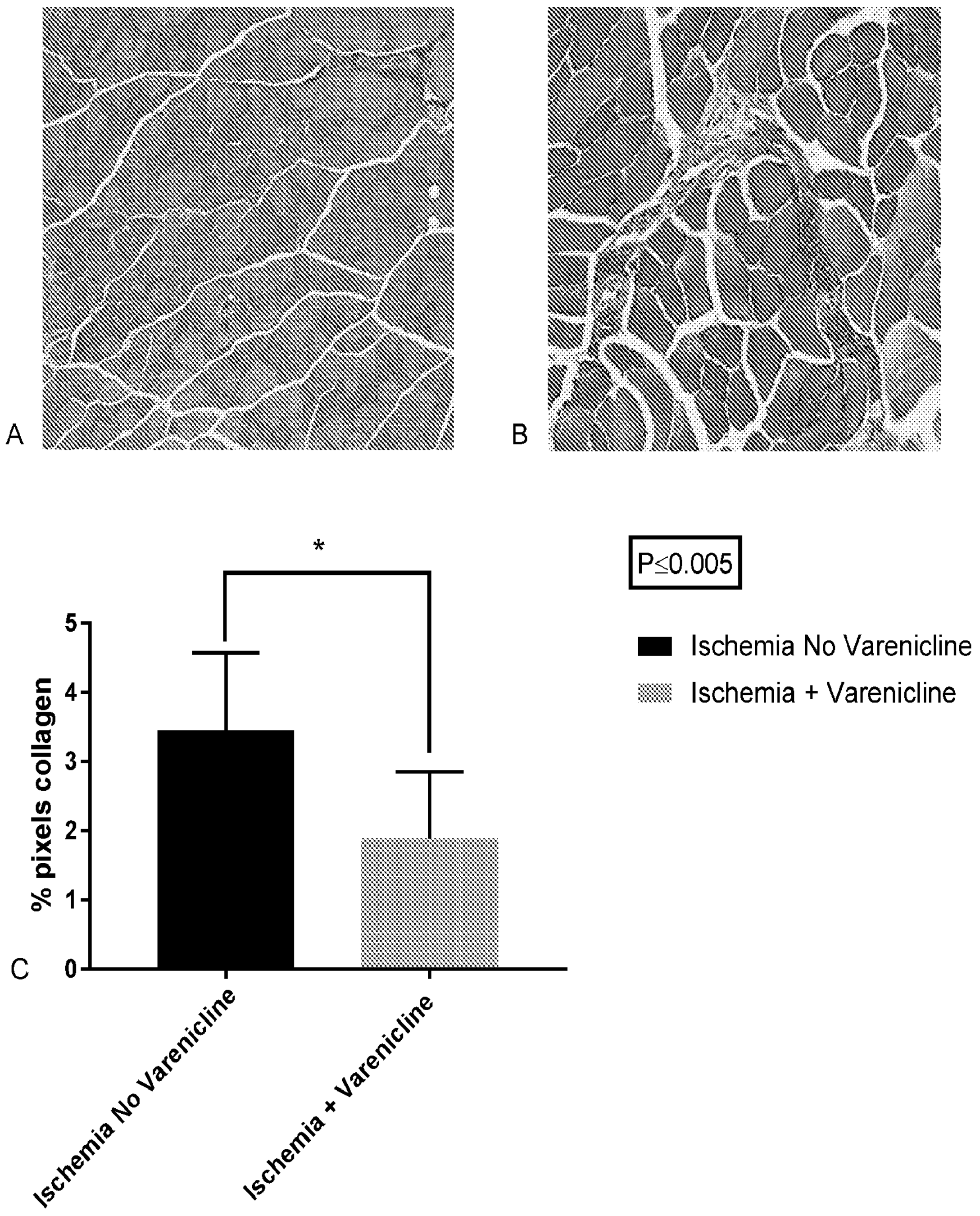
FIG. 9A-C shows trichrome staining of muscle fibers 14 days following limb ischemia in animals treated with varenicline (A), N=10 and untreated controls (B), N=10 Animals treated with varenicline demonstrated a significant decrease in collagen deposition in animals treated with varenicline (C) P≤0.005.
Figure 10:
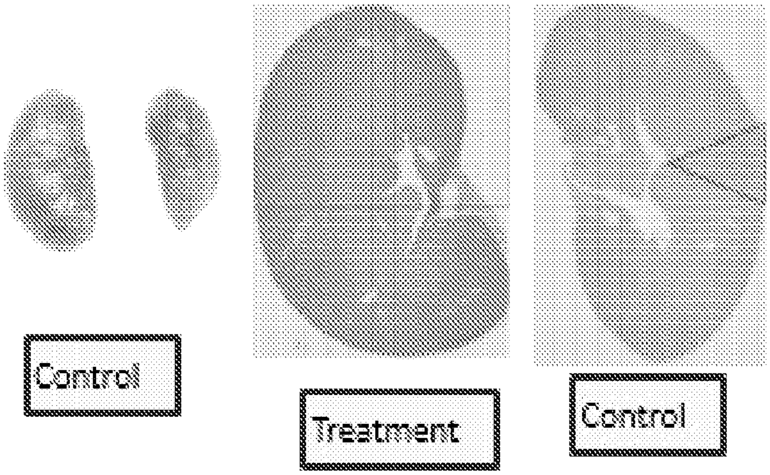
FIG. 10A-C shows evidence of renal scar formation and renal atrophy 30 days following acute pyelonephritis in a mouse. Preliminary results suggest that the incidence of scar formation and atrophy is decreased in animals treated with varenicline. A and C are controls, B shows treatment with varenicline.

In replicating the findings of Gigliotti et al. (2013), it was found that a single intraperitoneal injection of cytisine one hour prior to the surgical creation of testicular torsion decreases the number of CD45+ cells recruited to the testis 18 hours following reperfusion. (FIG. 1). Mice treated with cytisine an hour prior to the onset of testicular torsion also had increased levels reduced glutathione (FIG. 2) and decreased levels of myeloperoxidase activity reflecting a decrease in the innate immune response and oxidative stress when compared to untreated controls. Long term (30 day) outcomes following treatment with cytisine demonstrated decreased testicular atrophy, (FIG. 3), reduced histologic evidence of testicular fibrosis (FIG. 4), and decreased expression of pro-fibrotic genes (FIG. 5). These results confirm that as previously reported in the kidney (Gigliotti 2013), activation the cholinergic anti-inflammatory pathway with cytisine prior to the creation of testicular torsion limits ischemia reperfusion injury and prevents long term testicular atrophy and fibrosis.

Available as an aid to smoking cessation outside of the United States, Cytisine is not FDA approved for clinical use. Clinical activation of the CAP with cytisine is also technically difficult as cytisine levels achieved with therapeutic dosing do not activate α7nAChR26. Using and adoptive transfer model and α7nAChR knockout mice, Gigliotti et al (2013) definitively demonstrated that cytisine's immunosuppressive effects are mediated by the α7nAChR. In searching for a clinically applicable, FDA approved method of activating the CAP, Varenicline was identified as both a strong α4β2nAChR and α7nAChR agonist at systemic concentrations found with routine oral dosing in humans (Campling 2013). When varenicline was administered to mice 1 hour after the onset of testicular torsion, a reduction in the acute immune cell infiltrate (FIG. 1) was identified, increased levels of reduced glutathione (FIG. 2B), and decreased MPO activity (FIG. 2A) were also seen. Given the short half-life of 1.4 hours in mice (Obach 2006), varenicline was administered every 12 hours for a total of 4 doses in our long term (30 days) outcome group. Similar to the reported outcomes with cytisine, it was found that administration of varenicline 1 hour after the onset of testicular torsion preserved testicular weight (FIG. 3), and decreased histologic and genetic markers of testicular fibrosis (FIGS. 4 and 5).

Varenicline is currently FDA approved for use in adults, but it has also been studied as a smoking cessation aid in adolescents aged 12-16, which is also the peak incidence for testicular torsion. When administered to adolescents, there was a low incidence of neurocognitive side effects which occurred in 3 out of 75 patients and were limited to abnormal dreams in 2 patients and transient mild anger in 1 patient (Faessel 2009).

Evidence also suggests that cholinergic stimulation inhibits the ability of macrophages to secrete pro-inflammatory cytokines, but not the anti-inflammatory cytokine, IL-. Therefore, cytisine administration may alter the profile of recruited immune cells within the testis to promote healing rather than progression of IRI following torsion. In addition to its effects on immune effector cells, activation of the CAP with nicotine prevents immune cell recruitment by decreasing the expression of adhesion molecules such as E-selectin, ICAM-1 and VCAM-1 (Saeed 2005).

This report is the first to demonstrate that activation of a central immunosuppressive cascade with the nicotine analogs cytisine and varenicline limits ischemia reperfusion injury in a murine model of testicular torsion. Reduction in the ischemia reperfusion injury prevented long term testicular atrophy and fibrosis, identifying varenicline as useful in the management of testicular torsion.

Example 2: Varenicline Prevents Renal Ischemia Reperfusion Injury Following Pyelonephritis Summary Purpose: Renal insufficiency secondary to renal scaring and fibrosis is one of the feared long-term complications following pyelonephritis. Following the acute infection and innate immune response, ischemia reperfusion injury (IRI) has been found to be central to renal scar formation. While antibiotics are effective at treating the bacterial infection, they do little to affect the host immune response. The administration of corticosteroids has previously been shown to limit scar formation following pyelonephritis, however clinical application has been limited secondary to difficulty in selecting the appropriate patient population and systemic side effects. It is shown herein that varenicline, an α7 nAChR agonist, activates a central immunosuppressive cascade and limits ischemia reperfusion injury following testicular torsion. Varenicline can also decrease ischemia reperfusion injury and renal scar formation in a murinemodel of pyelonephritis.

Methods: Using an established murine model, pyelonephritis was induced by inoculating the bladder of C3H/HeOuJ mice with a uropathogenic *E. coli*. Five days following inoculation, half of the animals were treated with 5 days of ceftriaxone and half were treated with 5 days of ceftriaxone plus varenicline in the initial 48 hours. Histology and the expression of ischemia reperfusion injury markers and pro-fibrotic genes were evaluated at 14 and 30 days following the initial infection.

Results: At 14 days following the initial infection there was decreased expression of markers of ischemia reperfusion injury in animals treated with varenicline+ceftriaxone compared to those treated with ceftriaxone alone. Thirty day results also demonstrated a trend towards a decreased expression of pro-fibrotic genes in animals treated with varenicline in addition to ceftriaxone.

Conclusion: The initial results show that activation of a central immunosuppressive cascade with varenicline limits the innate immune response and long-term fibrosis following pyelonephritis. When compared to previously investigated immunosuppressive therapies, varenicline has limited side effects and can be effective in treating pyelonephritis.

Introduction

Acute pyelonephritis is a common pediatric condition that can confer a lifelong risk of hypertension, preeclampsia, and progressive renal failure due to renal fibrosis or "scarring." Interventions such as prophylactic antibiotics have reduced the incidence of recurrent pyelonephritis but have failed to decrease renal scar formation (Investigators 2014; Hewitt 2017) leaving "reflux nephropathy" as the 4th most common cause of pediatric renal transplantation (Shapiro 2010). While the cellular mechanisms have yet to be fully understood, inflammation from the innate immune response (Jang 2015; Svensson 2011; Hang 2000; Bille 1982; Meylan 1989) and subsequent ischemia reperfusion injury (IRI) (Li 2017) have emerged as key mediators of renal scar formation. Early trials have identified a promising reduction in the incidence of renal scars when pyelonephritis is treated with antibiotics and immunosuppressants such as corticosteroids (Huang 2011; Bahat 2014; Pohl 1999), non-steroidal anti-inflammatory medications (NSAIDs) (Bille 1982; Gurocak 2010) or anti-oxidants (Sadeghi 2008; Zhang 2016). Despite these encouraging results, a major knowledge gap exists as these therapies have limited clinical application.

Description of the cholinergic anti-inflammatory pathway (CAP) (Rosas 2011) has revealed a potentially novel therapeutic approach to limiting ischemia reperfusion injury. Alpha 7 nicotinic receptors (α7nAChr) are central to this pathway as their activation inhibits nuclear factor kappa-light-chain-enhancer of activated B cells (NF-κB) signaling and the intracellular response to pro-inflammatory cytokines (Tracey 2009). In addition to anti-inflammatory roles in conditions such as sepsis, peritonitis, and pancreatitis (Campling 2013; Murawski 2010; Bowen 2013), activation of the cholinergic anti-inflammatory pathway reduces IRI and prevents long term renal fibrosis following warm renal ischemia in the mouse (Gigliotti 2013). Pharmacologic activation of α7nAChR with the nicotinic agonist cytisine has been previously described in mice, but has limited clinical applicability as cytisine is not approved by the US Food and Drug Administration (FDA) and does not activate α7nAChR with systemic concentrations reached in routine dosing in humans (Campling 2013). α4β2nAChR agonist and smoking cessation aid varenicline (Chantix®) offers a novel approach as it also activates α7nAChR at concentrations achieved with therapeutic dosing (Campling 2013). It has been shown that administration of varenicline reduces ischemia reperfusion injury following testicular torsion, preventing long-term testicular atrophy and fibrosis. Disclosed herein is the treatment of pyelonephritis with antibiotics and varenicline, which reduces ischemia reperfusion injury and prevents long-term renal fibrosis.

Methods

Animals and Pyelonephritis Model

As previously described, female C3H/HeOuJ mice were utilized due to a high incidence of vesicoureteral reflux (VUR) (Li 2017; Murawski 2010; Bowen 2013) and reliable creation of pyelonephritis following bladder inoculation. To initiate pyelonephritis, the bladder was catheterized with a 24-gauge angiocatheter and a total volume of 100 μL of a phosphate-buffered saline containing 108 colony forming units (CFU) of CFT073 uropathogenic *Escherichia coli* (UPEC) was then instilled. Following the initial bladder inoculation, pyelonephritis was allowed to progress untreated for 5 days.

Following the initial 5-day incubation period, 2 mice were sacrificed to confirm infection. The remaining mice were then treated with ceftriaxone alone (control) or ceftriaxone with varenicline (treatment). All mice received 250 mg/kg of subcutaneous ceftriaxone administered twice daily for a period of 5 days. Animals in the treatment group also received a concurrent twice-daily dose of intraperitoneal varenicline (1 mg/kg) during the first 48 hours of treatment. Success of the antibiotic therapy was demonstrated in both control and treatment groups by the lack of bacterial growth from cultured kidneys harvested after the final dose of antibiotics. Animals were sacrificed at 14 days following the initial bladder inoculation to assess short-term outcomes, while long-term outcomes were assessed 30 days following initial bladder inoculation.

Histologic Analysis

Tissues were preserved in formalin for 72 hours then stored in ethanol. Sections were cut to a 5 μm thickness and stained with H&E or Masson trichrome. Photographs were obtained at 20× resolution with Olympus VS120 virtual slide microscope system. The images were then analyzed with ImageJ Fiji software in order to quantify collagen deposition as previously described (Chen 2017). As collagen deposition would be expected as long-term sequelae of IRI, the trichrome stains of the long-term specimen were examined. All artifacts from the staining process as well as gross collecting system were cropped from these images prior to analysis. A color deconvolution plugin was used to separate the trichrome images into the separate colors. Analysis was performed based upon the percentage of deposition of collagen in the green image compared to the overall area of the kidneys.

Real Time PCR

RNA was isolated from testis tissue using RNEasy mini kit (Qiagen, Hilden, Germany) per the manufacturer's protocol with the RNA concentration measured via Nanodrop 8000 (Thermo Scientific, Waltham, MA). cDNA was synthesized using Superscript First-Strand Synthesis system for Real-Time polymerase chain reaction (RT-PCR) (Invitrogen, Carlsbad, CA) on a GeneAmp PCR System 9700 (Applied Biosystems, Foster City, CA). Real-time PCR was performed using QuantStudio 7 Flex (Applied Biosystems, Foster City, CA) with Software Quantstudio Real-Time PCR Software (Thermo Fisher Scientific, Waltham, MA) and TaqMan Gene Expression Assays (Applied Biosystems, Foster City, CA). Standard TaqMan primers were used for Complement 1 q B chain (C1qb, Mm01179619_m1), Lipocalin 2 (Lcn2, Mm01324470_m1), Serpina (Mm04213318_m1), Cathepsin S (Ctss, Mm01255859_m1), Vascular cell adhesion molecule 1 (Vcam1, Mm01320970_m1), Interleukin 1 beta (IL-1β, Mm00434228_m1), and Nitric oxide synthase 2 (Nos2, Mm00440502_m1) as short-term IRI markers and Collagen 1 (Col1, Mm00801666_g1), Collagen 3 (Col3, Mm01254476_m1), Vimentin (Vim, Mm01333430_m1), and Smooth muscle actin (Acta, Mm00725412_s1) to evaluate long-term fibrosis.

Statistical Analysis

One-way ANOVA or Student's t-test was utilized as appropriate. Post hoc testing was performed with Bonferroni test. A p-value less than 0.05 was considered statistically significant.

Results

Figure 11:
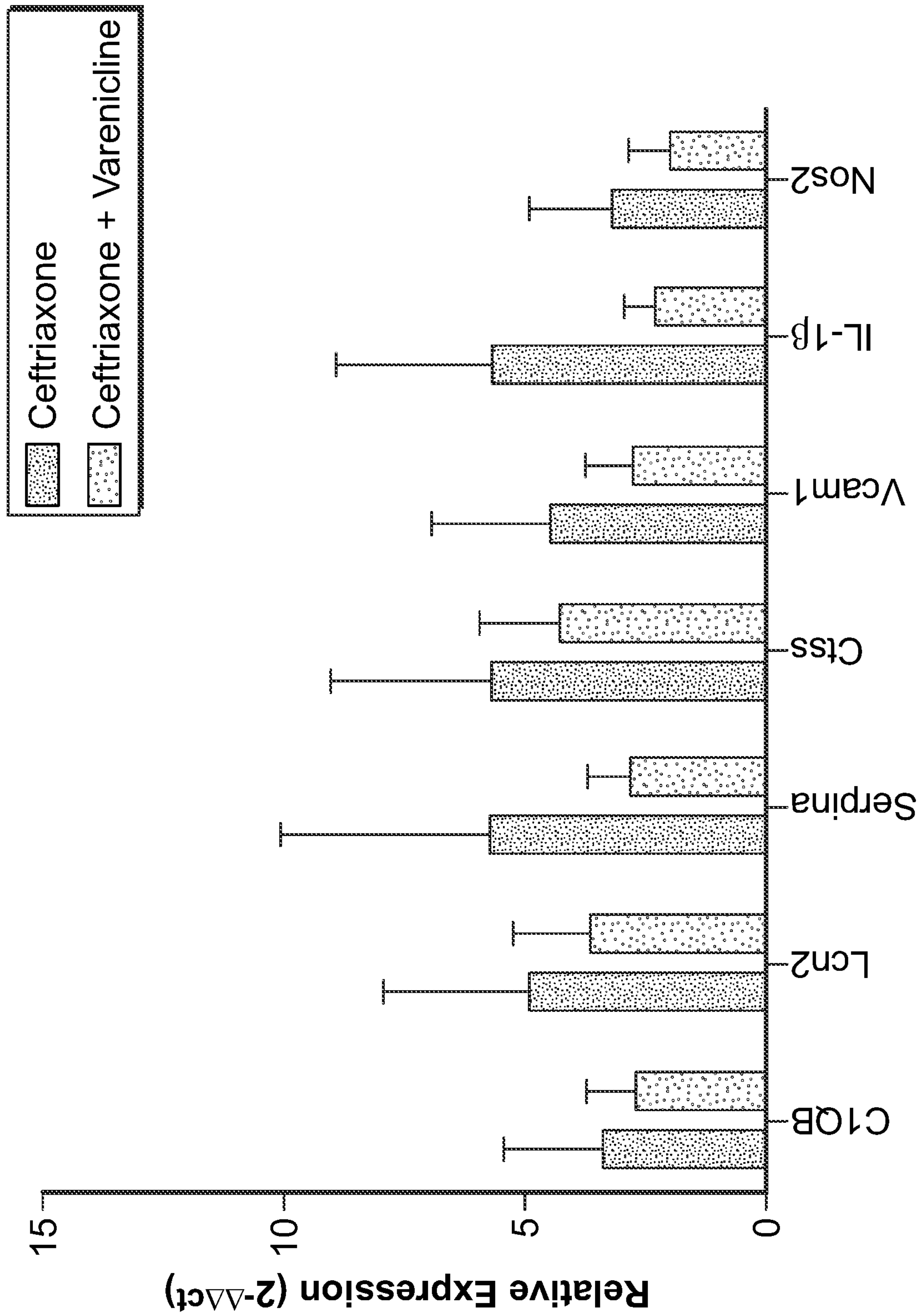
FIG. 11 Quantitative PCR performed 5 days after completion of antibiotic therapy demonstrates decreased expression of established mediators of IRI in animals treated with varenicline and ceftriaxone when compared to those treated with ceftriaxone alone.

Varenicline Administration Reduces Expression of Known IRI Mediators Following Acute Pyelonephritis Quantitative PCR 14 days after inoculation and 5 days after completion of antibiotic therapy demonstrated decreased expression of established mediators of renal ischemia reperfusion injury in animals treated with varenicline and ceftriaxone when compared to those treated with ceftriaxone alone (FIG. 11).

Figure 12:
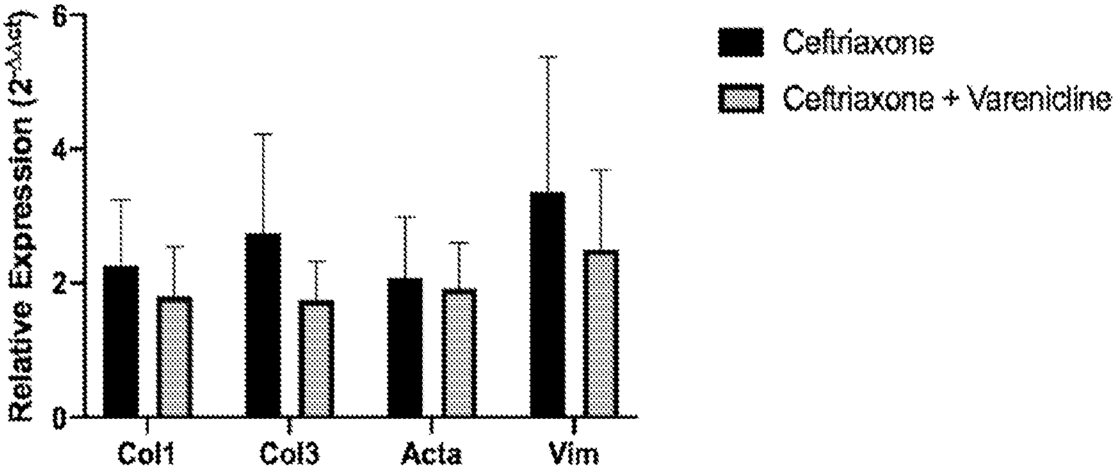
FIG. 12 shows kidneys removed from animals sacrificed at 30 days demonstrated a decrease in expression of genes responsible for renal fibrosis in animals treated with varenicline. Decrease in expression of vimentin in treated animals is significant with p-value of 0.03.

Expression of Genes Responsible for Fibrosis is Down-Regulated in Animals Treated with Varenicline Following Acute Pyelonephritis The expression of pro-fibrotic genes was investigated with quantitative PCR 30 days following inoculation and 21 days after completion of antibiotic therapy. Animals treated with ceftriaxone and varenicline demonstrated decreased expression of Col1, Col3, acta, and vimentin (FIG. 12).

Figure 13:
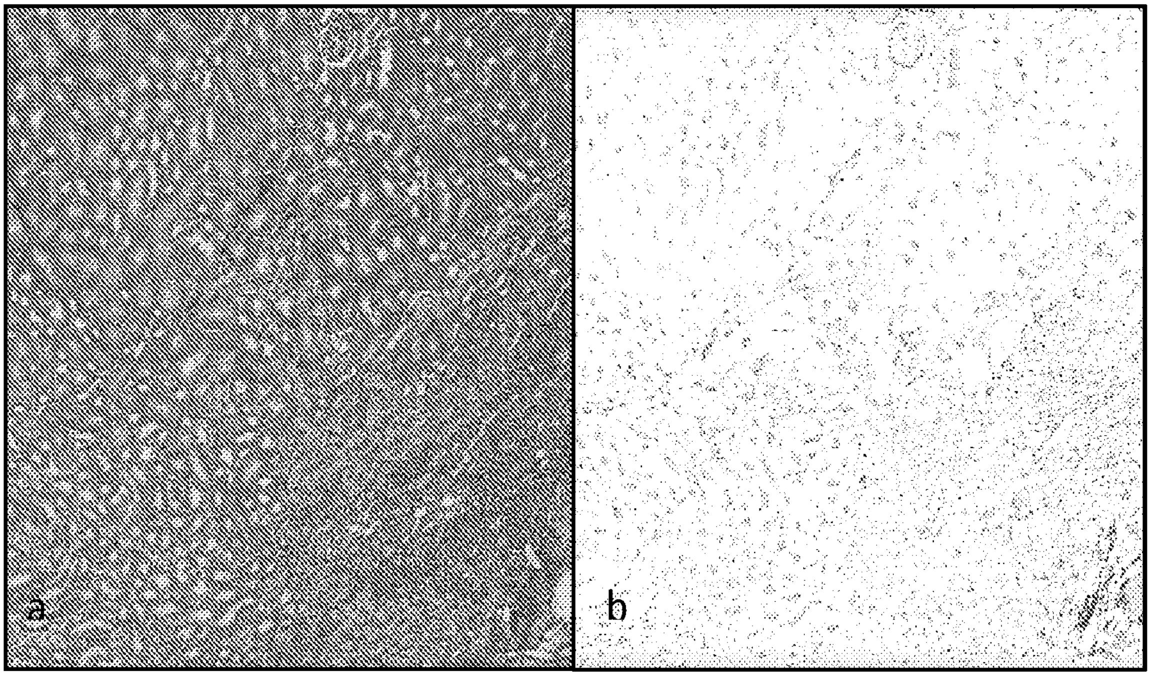
FIG. 13A-B shows: A) A representative 1 mm×1 mm section of a long-term kidney following trichrome staining. B) Following color deconvolution, an image is generated with only the green pigment. After setting a threshold to remove background artifact, the collagen is then highlighted in red.
Figure 14:
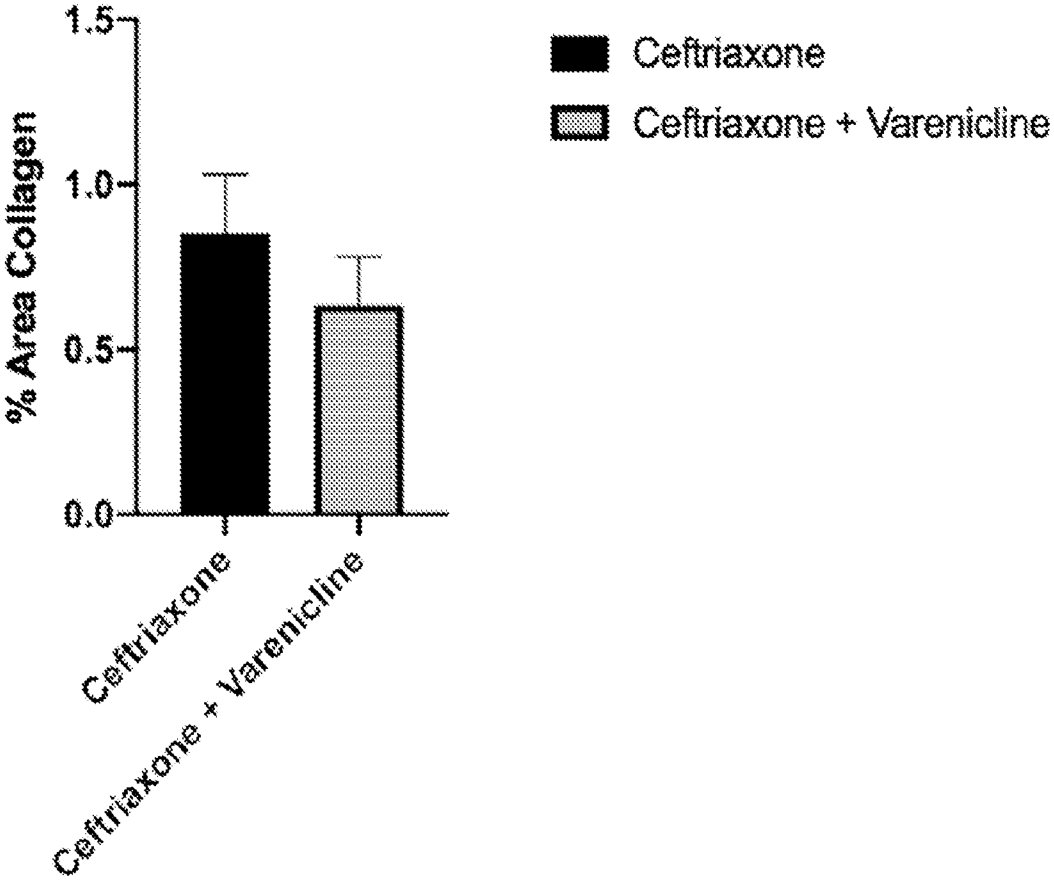
FIG. 14 shows following color deconvolution and collagen quantification in ImageJ, collagen was defined as a percentage of green pigment per the area of the entire kidney with the exception of the obvious collecting system. Collagen deposition is significantly higher in animals treated with ceftriaxone alone (p=0.001).

Treatment with Varenicline Results in Decreased Collagen Deposition in the Renal Parenchyma Histologically Following Acute Pyelonephritis Tissues harvested 21 days following completion of antibiotic therapy were subjected to trichome staining to assess for global collagen deposition. After removing artifacts (to ensure only parenchyma was included in the analysis), a color deconvolution plugin was used for ImageJ to divide the images into the respective three colors of the trichrome stain. A threshold was set and collagen was quantified as a percentage of green color in respect to the area of the entire kidney (FIG. 13). Animals who were treated with varenicline in addition to antibiotics demonstrated a significantly lower amount of collagen deposition in the kidneys in comparison to animals that were treated with antibiotics alone ($p=0.001$) (FIG. 14).

Discussion

Vesicoureteral reflux is the most common risk factor for recurrent pyelonephritis. Despite a reduction in the incidence of recurrent infections, interventions such as prophylactic antibiotics have yet to demonstrate a decrease in the incidence of renal scars (Hewitt 2017), leaving a large population of children at risk for long term complications including hypertension, pre-eclampsia, and end-stage renal disease. Small studies targeting the host immune response with corticosteroids, NSAIDs and antioxidants (Gurocak 2010; Zhang 2016; Sobouti 2013; Huang 2011; Ghaffari 2019; Imamoglu 2006) have demonstrated a promising reduction in renal scars, but have limited clinical applicability due to systemic side effects and the use of non-FDA regulated compounds.

Activation of the cholinergic anti-inflammatory pathway with varenicline has can prevent IRI, including a decrease in IRI following testicular torsion in animals treated with varenicline. Unlike the previously studied medications as listed above, varenicline has been found to have minimal side effects in an adolescent population (Faessel 2006). The anti-inflammatory effects of varenicline can limit ischemia reperfusion injury following acute bacterial pyelonephritis, preventing long term renal fibrosis and scarring.

Acute pyelonephritis results in a robust innate immune response and up-regulation of ischemia reperfusion pathways which have been postulated to be central to mediating renal scar formation (Li 2017). In this experiment, animals treated with varenicline in addition to ceftriaxone demonstrated a decreased expression of IRI markers 5 days after completion of antibiotic therapy. The difference between the two groups was not statistically significant, however there was a clear trend across multiple genes (FIG. 11).

Treatment with varenicline also resulted in a long-term decrease in collagen deposition and expression of pro-fibrotic genes 21 days after the completion of antibiotic therapy. Together these results demonstrate that the administration of varenicline in addition to antibiotics reduces acute inflammation and limits long-term renal fibrosis in a murine model of pyelonephritis. 14.

Abbreviations

α7nAchR α7 nicotinic acetylcholine receptor
Acta Smooth muscle actin
AKI Acute kidney injury APN Acute bacterial pyelonephritis
C1qb Complement C1q B chain
CAP Cholinergic anti-inflammatory pathway
CFU Colony forming units
CKD Chronic kidney disease
Colla3 (or Col1) Collagen 1
Col3a3 (or Col3) Collagen 3
Ctss Cathepsin S
EC50 Half maximal effective concentration
FACS Fluorescence-activated cell sorting
FDA US Food and Drug Administration
HIF3α Hypoxia inducible factor 3α
IL-1β Interleukin 1 beta
IL-6 Interleukin-6
IRI Ischemia reperfusion injury
Lcn2 Lipocalin 2
MPO Myeloperoxidase
NF-κB Nuclear factor Kappa Beta
Nos2 Nitric oxide synthase 2
NSAIDs Non-steroidal anti-inflammatory medications
RT-PCR Real-time polymerase chain reaction
ROS Reactive oxygen species
Sma Smooth muscle actin
TLR4 Toll-like receptor 4
TNFα Tumor necrosis factor alpha
UPEC Uropathogenic *Escherichia coli*
Vcam1 Vascular cell adhesion molecule 1
Vim Vimentin
VUR Vesicoureteral reflux

REFERENCES

1. Zhao L C, Lautz T B, Meeks J J, Maizels M. Pediatric testicular torsion epidemiology using a national database: incidence, risk of orchiectomy and possible measures toward improving the quality of care. *The Journal of urology.* 2011; 186:2009-2013.
2. Sessions A E, Rabinowitz R, Hulbert W C, Goldstein M M, Mevorach R A. Testicular torsion: direction, degree, duration and disinformation. *The Journal of urology.* 2003; 169:663-665.
3. Tryfonas G, Violaki A, Tsikopoulos G, et al. Late post-operative results in males treated for testicular torsion during childhood. *Journal of pediatric surgery.* 1994; 29:553-556.
4. Visser A J, Heyns C F. Testicular function after torsion of the spermatic cord. *BJU international.* 2003; 92:200-203.
5. Anderson J B, Williamson R C. The fate of the human testes following unilateral torsion of the spermatic cord. *British journal of urology.* 1986; 58:698-704.
6. Anderson M J, Dunn J K, Lipshultz L I, Coburn M. Semen quality and endocrine parameters after acute testicular torsion. *The Journal of urology.* 1992; 147:1545-1550.
7. Krarup T. The testes after torsion. *British journal of urology.* 1978; 50:43-46.
8. Wei S M, Yan Z Z, Zhou J. Beneficial effect of taurine on testicular ischemia-reperfusion injury in rats. *Urology.* 2007; 70:1237-1242.
9. Wei S M, Yan Z Z, Zhou J. Protective effect of rutin on testicular ischemia-reperfusion injury. *Journal of pediatric surgery.* 2011; 46:1419-1424.
10. Wei S M, Huang Y M, Zhou J. Probucol Reduces Testicular Torsion/Detorsion-Induced Ischemia/Reperfusion Injury in Rats. *Oxid Med Cell Longev.* 2017; 2017: 5424097.
11. Ozbek O, Altintas R, Polat A, et al. The protective effect of apocynin on testicular ischemia-reperfusion injury. *The Journal of urology.* 2015; 193:1417-1422.
12. Qi X, Qin Z, Tang J, et al. Omega-3 polyunsaturated fatty acids ameliorates testicular ischemia-reperfusion injury through the induction of Nrf2 and inhibition of NF-κB in rats. *Experimental and Molecular Pathology.* 2017; 103:44-50.
13. Semercioz A, Baltaci A K, Mogulkoc R, Avunduk M C. Effect of Zinc and Melatonin on Oxidative Stress and Serum Inhibin-B Levels in a Rat Testicular Torsion-Detorsion Model. *Biochemical genetics.* 2017; 55:395-409.
14. Yapanoglu T, Ozkaya F, Yilmaz A H, et al. Effect of etoricoxib on experimental oxidative testicular ischemia-reperfusion damage in rats induced with torsion-detorsion. *Korean J Physiol Pharmacol.* 2017; 21:457-464.
15. Ghasemnejad-Berenji M, Ghazi-Khansari M, Yazdani I, et al. Rapamycin protects testes against germ cell apoptosis and oxidative stress induced by testicular ischemia-reperfusion. *Iran J Basic Med Sci.* 2017; 20:905-911.
16. Ning J Z, Li W, Cheng F, et al. MiR-29a Suppresses Spermatogenic Cell Apoptosis in Testicular Ischemia-Reperfusion Injury by Targeting TRPV4 Channels. *Front Physiol.* 2017; 8:966.
17. Lysiak J J, Turner S D, Nguyen Q A, Singbartl K, Ley K, Turner T T. Essential role of neutrophils in germ cell-specific apoptosis following ischemia/reperfusion injury of the mouse testis. *Biology of reproduction.* 2001; 65:718-725.
18. Rosas-Ballina M, Olofsson P S, Ochani M, et al. Acetylcholine-synthesizing T cells relay neural signals in a vagus nerve circuit. *Science.* 2011; 334:98-101.
19. Huston J M, Ochani M, Rosas-Ballina M, et al. Splenectomy inactivates the cholinergic antiinflammatory pathway during lethal endotoxemia and polymicrobial sepsis. *The Journal of experimental medicine.* 2006; 203: 1623-1628.
20. Wang H, Liao H, Ochani M, et al. Cholinergic agonists inhibit HMGB1 release and improve survival in experimental sepsis. *Nature medicine.* 2004; 10:1216-1221.
21. van Westerloo D J, Giebelen I A, Florquin S, et al. The vagus nerve and nicotinic receptors modulate experimental pancreatitis severity in mice. *Gastroenterology.* 2006; 130:1822-1830.
22. Andersson U, Tracey K J. Neural reflexes in inflammation and immunity. *The Journal of experimental medicine.* 2012; 209:1057-1068.
23. Gigliotti J C, Huang L, Ye H, et al. Ultrasound prevents renal ischemia-reperfusion injury by stimulating the splenic cholinergic anti-inflammatory pathway. *Journal of the American Society of Nephrology: JASN.* 2013; 24:1451-1460.
24. Sadis C, Teske G, Stokman G, et al. Nicotine protects kidney from renal ischemia/reperfusion injury through the cholinergic anti-inflammatory pathway. *PloS one.* 2007; 2:e469.
25. Yeboah M M, Xue X, Duan B, et al. Cholinergic agonists attenuate renal ischemia-reperfusion injury in rats. *Kidney international.* 2008; 74:62-69.
26. Campling B G, Kuryatov A, Lindstrom J. Acute activation, desensitization and smoldering activation of human acetylcholine receptors. *PloS one.* 2013; 8:e79653.
27. Caetano G F, Fronza M, Leite M N, Gomes A, Frade M A. Comparison of collagen content in skin wounds evaluated by biochemical assay and by computer-aided histomorphometric analysis. *Pharmaceutical biology.* 2016; 54:2555-2559.

28. Lysiak J J, Nguyen Q A, Turner T T. Peptide and nonpeptide reactive oxygen scavengers provide partial rescue of the testis after torsion. *Journal of andrology.* 2002; 23:400-409.
29. Turner T T, Tung K S, Tomomasa H, Wilson L W. Acute testicular ischemia results in germ cell-specific apoptosis in the rat. *Biology of reproduction.* 1997; 57:1267-1274.
30. Suzuki T, Hide I, Matsubara A, et al. Microglial alpha7 nicotinic acetylcholine receptors drive a phospholipase C/IP3 pathway and modulate the cell activation toward a neuroprotective role. *Journal of neuroscience research.* 2006; 83:1461-1470.
31. Shytle R D, Mori T, Townsend K, et al. Cholinergic modulation of microglial activation by alpha 7 nicotinic receptors. *Journal of neurochemistry.* 2004; 89:337-343.
32. Yoshikawa H, Kurokawa M, Ozaki N, et al. Nicotine inhibits the production of proinflammatory mediators in human monocytes by suppression of I-kappaB phosphorylation and nuclear factor-kappaB transcriptional activity through nicotinic acetylcholine receptor alpha7. *Clin Exp Immunol.* 2006; 146:116-123.
33. de Jonge W J, van der Zanden E P, The F O, et al. Stimulation of the vagus nerve attenuates macrophage activation by activating the Jak2-STAT3 signaling pathway. *Nature immunology.* 2005; 6:844-851.
34. Parrish W R, Rosas-Ballina M, Gallowitsch-Puerta M, et al. Modulation of TNF release by choline requires alpha7 subunit nicotinic acetylcholine receptor-mediated signaling. *Molecular medicine* (*Cambridge, Mass.*). 2008; 14:567-574.
35. Rosas-Ballina M, Ochani M, Parrish W R, et al. Splenic nerve is required for cholinergic antiinflammatory pathway control of TNF in endotoxemia. *Proceedings of the National Academy of Sciences of the United States of America.* 2008; 105:11008-11013.
36. Obach R S, Reed-Hagen A E, Krueger S S, et al. Metabolism and disposition of varenicline, a selective alpha4beta2 acetylcholine receptor partial agonist, in vivo and in vitro. *Drug metabolism and disposition: the biological fate of chemicals.* 2006; 34:121-130.
37. Faessel H, Ravva P, Williams K. Pharmacokinetics, safety, and tolerability of varenicline in healthy adolescent smokers: a multicenter, randomized, double-blind, placebo-controlled, parallel-group study. *Clinical therapeutics.* 2009; 31:177-189.
38. Anthenelli R M, Benowitz N L, West R, et al. Neuropsychiatric safety and efficacy of varenicline, bupropion, and nicotine patch in smokers with and without psychiatric disorders (EAGLES): a double-blind, randomised, placebo-controlled clinical trial. *Lancet.* 2016; 387:2507-2520.
39. Ulloa L. The vagus nerve and the nicotinic anti-inflammatory pathway. *Nature reviews. Drug discovery.* 2005; 4:673-684.
40. Saeed R W, Varma S, Peng-Nemeroff T, et al. Cholinergic stimulation blocks endothelial cell activation and leukocyte recruitment during inflammation. *The Journal of experimental medicine.* 2005; 201:1113-1123.
41. Kalogeris, T., et al. (2014). "Mitochondrial reactive oxygen species: A double edged sword in ischemia/reperfusion vs preconditioning." Redox biology 2: 702-714.
42, Caetano, G. F., et al. (2016). "Comparison of collagen content in skin wounds evaluated by biochemical assay and by computer-aided histomorphometric analysis." Pharm Biol 54(11): 2555-2559.
43. Gigliotti, J. C., et al. (2013). "Ultrasound prevents renal ischemia-reperfusion injury by stimulating the splenic cholinergic anti-inflammatory pathway." J Am Soc Nephrol 24(9): 1451-1460.
44. Sadis, C., et al. (2007). "Nicotine protects kidney from renal ischemia/reperfusion injury through the cholinergic anti-inflammatory pathway." PLoS One 2(5): e469.
45. Yeboah, M. M., et al. (2008). "Cholinergic agonists attenuate renal ischemia-reperfusion injury in rats." Kidney Int 74(1): 62-69.

What is claimed is:

1. A method of treating a subject with ischemia reperfusion injury or at risk of developing ischemia reperfusion injury in one or more tissues or organs, the method comprising administering to the subject an agonist of nicotinic cholinergic receptor α7nAchR, wherein the subject has, or is at risk of developing, testicular torsion, wherein the method reduces or prevents long-term fibrosis and/or long-term atrophy in the one or more tissues or organs, and wherein long-term fibrosis and/or long-term atrophy is measured at least 30 days following testicular torsion.

2. The method of claim 1, wherein the agonist comprises varenicline or a derivative thereof.

3. The method of claim 1, wherein the subject is at risk of developing ischemia reperfusion injury, and administration of the agonist prevents ischemia reperfusion injury; or wherein the subject is diagnosed with ischemia prior to administration of the agonist.

4. The method of claim 1, wherein the subject is undergoing or is scheduled to undergo a procedure that can induce ischemia.

5. The method of claim 1, wherein at least a first dose of the agonist is administered in a clinical setting.

6. The method of claim 1, wherein the subject is monitored for ischemia reperfusion injury before, after, and/or during administration of the agonist.

7. The method of claim 1, wherein the subject is under 18 years old.

8. The method of claim 1, wherein the subject is also treated with one or more additional anti-inflammatory compositions and/or antioxidants.

9. The method of claim 1, wherein the subject is not in a clinically prescribed smoking cessation program while being treated for ischemia perfusion injury.

10. The method of claim 1, wherein the subject receives 10 or less doses of an agonist of nicotinic cholinergic receptor α7nAchR during an entire course of treatment.

11. The method of claim 1, wherein the subject has an infection, has the risk of developing an infection, or is diagnosed with an infection prior to administration of the agonist, and wherein the infection is septic or bacterial.

12. The method of claim 1, wherein the subject has an inflammation, has the risk of developing inflammation, or is diagnosed with inflammation prior to administration of the agonist, wherein organ dysfunction of the subject is caused by systemic inflammatory response, and wherein the systemic inflammatory response is cytokine storm.

13. The method of claim 2, wherein the varenicline comprises 7,8,9,10-tetrahydro-6, 10-methano-6H-pyrazino [2,3-h][3]benzazepine (varenicline tartrate).

* * * * *